United States Patent
Chen

(10) Patent No.: US 10,849,888 B2
(45) Date of Patent: *Dec. 1, 2020

(54) ANTI-ANDROGENS FOR THE TREATMENT OF NON-METASTATIC CASTRATE-RESISTANT PROSTATE CANCER

(71) Applicant: Aragon Pharmaceuticals, Inc., San Diego, CA (US)

(72) Inventor: Isan Chen, San Diego, CA (US)

(73) Assignee: Aragon Pharmaceuticals, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/033,432

(22) Filed: Jul. 12, 2018

(65) Prior Publication Data

US 2018/0318277 A1 Nov. 8, 2018

Related U.S. Application Data

(63) Continuation of application No. 15/851,444, filed on Dec. 21, 2017, now Pat. No. 10,052,314, which is a continuation of application No. 14/034,460, filed on Sep. 23, 2013, now Pat. No. 9,884,054.

(60) Provisional application No. 61/705,900, filed on Sep. 26, 2012.

(51) Int. Cl.
*A61K 31/4439* (2006.01)
*A61K 31/4166* (2006.01)
*A61K 31/00* (2006.01)

(52) U.S. Cl.
CPC .......... *A61K 31/4439* (2013.01); *A61K 31/00* (2013.01); *A61K 31/4166* (2013.01); *H05K 999/99* (2013.01)

(58) Field of Classification Search
CPC .................... A61K 31/4439; A61K 31/4166
See application file for complete search history.

(56) References Cited

U.S. PATENT DOCUMENTS

| | | | |
|---|---|---|---|
| 3,798,233 A | 3/1974 | Akiba et al. |
| 3,823,240 A | 7/1974 | Sauli |
| 3,984,430 A | 10/1976 | Curran |
| 4,097,578 A | 6/1978 | Perronnet et al. |
| 4,229,447 A | 10/1980 | Porter |
| 4,234,736 A | 11/1980 | Bernauer et al. |
| 4,304,782 A | 12/1981 | Dumont et al. |
| 4,312,881 A | 1/1982 | Wootton |
| 4,399,216 A | 8/1983 | Axel et al. |
| 4,407,814 A | 10/1983 | Bernauer et al. |
| 4,427,438 A | 1/1984 | Nagano et al. |
| 4,473,393 A | 9/1984 | Nagpal |
| 4,482,739 A | 11/1984 | Bernauer et al. |
| 4,559,157 A | 12/1985 | Smith et al. |
| 4,596,795 A | 6/1986 | Pitha |
| 4,608,392 A | 8/1986 | Jacquet et al. |
| 4,749,403 A | 6/1988 | Liebl et al. |
| 4,755,386 A | 7/1988 | Hsiao et al. |
| 4,820,508 A | 4/1989 | Wortzman |
| 4,859,228 A | 8/1989 | Prisbylla |
| 4,873,256 A | 10/1989 | Coussediere et al. |
| 4,938,949 A | 7/1990 | Borch et al. |
| 4,944,791 A | 7/1990 | Schroeder et al. |
| 4,992,478 A | 2/1991 | Geria |
| 5,010,182 A | 4/1991 | Brake et al. |
| 5,011,692 A | 4/1991 | Fujioka et al. |
| 5,017,381 A | 5/1991 | Maruyama et al. |
| 5,033,252 A | 7/1991 | Carter |
| 5,052,558 A | 10/1991 | Carter |
| 5,069,711 A | 12/1991 | Fischer et al. |
| 5,071,773 A | 12/1991 | Evans et al. |
| 5,166,358 A | 11/1992 | Seuron et al. |
| 5,229,135 A | 7/1993 | Philippon et al. |
| 5,323,907 A | 6/1994 | Kalvelage |
| 5,411,981 A | 5/1995 | Gaillard-Kelly et al. |
| 5,434,176 A | 7/1995 | Claussner et al. |
| 5,554,607 A | 9/1996 | Elokdah et al. |
| 5,556,983 A | 9/1996 | Claussner et al. |
| 5,589,497 A | 12/1996 | Claussner et al. |
| 5,614,620 A | 3/1997 | Liao et al. |
| 5,627,201 A | 5/1997 | Gaillard-Kelly et al. |
| 5,646,172 A | 7/1997 | Claussner et al. |
| 5,656,651 A | 8/1997 | Sovak et al. |
| 5,705,654 A | 1/1998 | Claussner et al. |
| 5,726,061 A | 3/1998 | Robbins et al. |
| 5,738,685 A | 4/1998 | Halm et al. |
| 5,739,136 A | 4/1998 | Ellinwood et al. |
| 5,750,553 A | 5/1998 | Claussner et al. |
| 5,783,707 A | 7/1998 | Elokdah et al. |
| RE35,956 E | 11/1998 | Gaillard-Kelly et al. |

(Continued)

FOREIGN PATENT DOCUMENTS

| AU | 217893 | 6/1958 |
|---|---|---|
| AU | 2013323861 A1 | 4/2015 |

(Continued)

OTHER PUBLICATIONS

Madan et al. (2008). Analysis of Overall Survival in Patients with Nonmetastatic Castration-Resistant Prostate Cancer Treated with Vaccine, Nilutamide, and Combination Therapy. Cancer Therapy: Clinical, vol. 14(14), pp. 4526-4531.

Le et al. (2003). Plant-derived 3,3'-diindolylmethane Is a Strong Androgen Antagonist in Human Prostatic Cancer Cells. The Journal of Biological Chemistry, vol. 278(23), pp. 21136-21145.

Cook, "Development of GnRH Antagonists for Prostate Cancer: New Approaches to Treatment", The Oncologist Fundamentals of Cancer Medicine, 2000, vol. 5, 162-168.

Clegg et al., "ARN509: A Novel Antiandrogen for Prostate Cancer Treatment", Cancer Research, 2012, 72(6), 1494-1503.

(Continued)

*Primary Examiner* — San Ming R Hui
(74) *Attorney, Agent, or Firm* — BakerHostetler

(57) ABSTRACT

Described herein are methods of treating non-metastatic castrate-resistant prostate cancer with anti-androgens.

15 Claims, No Drawings

(56) References Cited

U.S. PATENT DOCUMENTS

| | | |
|---|---|---|
| 5,837,284 A | 11/1998 | Mehta et al. |
| 5,840,329 A | 11/1998 | Bai |
| 5,958,936 A | 9/1999 | Claussner et al. |
| 5,968,875 A | 10/1999 | Bis et al. |
| 5,985,868 A | 11/1999 | Gray |
| 6,107,488 A | 8/2000 | Bouchet et al. |
| 6,172,076 B1 | 1/2001 | Embrey et al. |
| 6,235,910 B1 | 5/2001 | Beller et al. |
| 6,242,611 B1 | 6/2001 | Claussner et al. |
| 6,307,030 B1 | 10/2001 | French et al. |
| 6,350,763 B1 | 2/2002 | Kelly et al. |
| 6,472,415 B1 | 10/2002 | Sovak et al. |
| 6,479,063 B2 | 11/2002 | Weisman et al. |
| 6,489,163 B1 | 12/2002 | Roy et al. |
| 6,506,607 B1 | 1/2003 | Shyjan |
| 6,710,037 B2 | 3/2004 | Wang et al. |
| 6,828,471 B2 | 12/2004 | Sawyers et al. |
| 7,271,188 B2 | 9/2007 | Tachibana et al. |
| 7,709,517 B2 | 5/2010 | Sawyers et al. |
| 8,183,274 B2 | 5/2012 | Sawyers et al. |
| 8,445,507 B2 | 5/2013 | Jung et al. |
| 8,461,343 B2 | 6/2013 | Ouerfelli et al. |
| 8,470,829 B2 | 6/2013 | Tachibana et al. |
| 8,802,689 B2 | 8/2014 | Jung et al. |
| 8,987,452 B2 | 3/2015 | Ouerfelli et al. |
| 9,108,944 B2 | 8/2015 | Smith et al. |
| 9,126,941 B2 | 9/2015 | Sawyers et al. |
| 9,289,436 B2 | 3/2016 | Szmulewitz et al. |
| 9,340,524 B2 | 5/2016 | Chen et al. |
| 9,388,159 B2 | 7/2016 | Jung et al. |
| 9,481,664 B2 | 11/2016 | Smith et al. |
| 9,512,103 B2 | 12/2016 | Ouerfelli et al. |
| 9,675,586 B2 | 6/2017 | Chow et al. |
| 9,884,054 B2 | 2/2018 | Chen |
| 10,052,314 B2 | 8/2018 | Chen |
| 2002/0133833 A1 | 9/2002 | Sawyers et al. |
| 2003/0225138 A1 | 12/2003 | Sircar et al. |
| 2004/0009969 A1 | 1/2004 | Cleve et al. |
| 2004/0077605 A1 | 4/2004 | Salvati et al. |
| 2004/0116417 A1 | 6/2004 | Boubia et al. |
| 2005/0153968 A1 | 7/2005 | Bi et al. |
| 2006/0025589 A1 | 2/2006 | Binet et al. |
| 2006/0127902 A1 | 6/2006 | Madden et al. |
| 2007/0004753 A1 | 1/2007 | Sawyers et al. |
| 2007/0249697 A1 | 10/2007 | Tachibana et al. |
| 2008/0032935 A1 | 2/2008 | Engel et al. |
| 2010/0190991 A1 | 7/2010 | Ouerfelli et al. |
| 2011/0003839 A1 | 1/2011 | Jung et al. |
| 2013/0045204 A1 | 2/2013 | Andersen et al. |
| 2013/0072511 A1 | 3/2013 | Jung et al. |
| 2013/0079241 A1 | 3/2013 | Luo et al. |
| 2013/0116258 A1 | 5/2013 | Smith et al. |
| 2013/0225821 A1 | 8/2013 | Ouerfelli et al. |
| 2013/0253035 A1 | 9/2013 | McDonnell et al. |
| 2014/0088129 A1 | 3/2014 | Chen |
| 2014/0314860 A1 | 10/2014 | Shah et al. |
| 2015/0133481 A1 | 5/2015 | Dilhas et al. |
| 2018/0318277 A1 | 11/2018 | Chen |
| 2019/0269667 A1 | 9/2019 | Chen |
| 2019/0269668 A1 | 9/2019 | Chen |

FOREIGN PATENT DOCUMENTS

| | | |
|---|---|---|
| CN | 101032483 A | 9/2007 |
| CN | 101032486 A | 9/2007 |
| CN | 104661658 A | 5/2015 |
| CN | 104857157 A | 8/2015 |
| DE | 2102605 | 7/1971 |
| DE | 2614831 | 10/1977 |
| EA | 030128 | 6/2018 |
| EP | 0002259 A2 | 6/1979 |
| EP | 0017976 A2 | 10/1980 |
| EP | 0144098 A1 | 6/1985 |
| EP | 0331232 A2 | 9/1989 |
| EP | 0362179 A2 | 4/1990 |
| EP | 0494819 A1 | 7/1992 |
| EP | 0572191 A1 | 12/1993 |
| EP | 0578516 A1 | 1/1994 |
| EP | 0580459 A1 | 1/1994 |
| EP | 0721944 A1 | 7/1996 |
| EP | 0770613 A1 | 5/1997 |
| EP | 1632477 A1 | 3/2006 |
| EP | 1790640 A1 | 5/2007 |
| EP | 2900224 A1 | 8/2015 |
| EP | 3305285 A1 | 4/2018 |
| FR | 2693461 A1 | 1/1994 |
| FR | 2715402 A1 | 7/1995 |
| FR | 2845384 A1 | 4/2004 |
| HK | 1212221 A1 | 6/2016 |
| HU | 217893 | 5/2000 |
| ID | 2016/03647 | 5/2016 |
| JP | 59-210083 A | 11/1984 |
| JP | 60-239737 A | 11/1985 |
| JP | 64-009978 A | 1/1989 |
| JP | 02-019363 A | 1/1990 |
| JP | 08-009997 | 1/1996 |
| JP | 2845384 B2 | 1/1999 |
| JP | 2003-530348 | 10/2003 |
| JP | 2004-525175 | 8/2004 |
| JP | 2004-252175 A | 9/2004 |
| JP | 2006-022118 A | 1/2006 |
| JP | 2006-510600 | 3/2006 |
| JP | 2006-265244 A | 10/2006 |
| JP | 2008-512419 A | 4/2008 |
| JP | 2008-099977 A | 5/2008 |
| JP | 2008-540523 | 11/2008 |
| JP | 2009-531439 | 9/2009 |
| JP | 2010-500975 A | 1/2010 |
| JP | 2010-504307 A | 2/2010 |
| JP | 2011-503075 A | 1/2011 |
| JP | 2011-068653 A | 4/2011 |
| JP | 2012-211190 A | 11/2012 |
| JP | 2012-236843 A | 12/2012 |
| JP | 5133975 B2 | 1/2013 |
| JP | 2015-534582 A | 12/2015 |
| JP | 2016-508991 A | 3/2016 |
| JP | 6351597 B2 | 7/2018 |
| JP | 2018-150365 A | 9/2018 |
| MX | 2015003909 A | 1/2016 |
| NZ | 705815 A | 8/2018 |
| UA | 117663 | 9/2018 |
| WO | 90/13646 A1 | 11/1990 |
| WO | 97/00071 A1 | 1/1997 |
| WO | 97/13646 A1 | 4/1997 |
| WO | 97/19064 A1 | 5/1997 |
| WO | 97/19931 A1 | 6/1997 |
| WO | 00/17163 A1 | 3/2000 |
| WO | 00/26195 A1 | 5/2000 |
| WO | 00/44731 A1 | 8/2000 |
| WO | 01/07048 A1 | 2/2001 |
| WO | 01/92253 A2 | 12/2001 |
| WO | 01/94346 A1 | 12/2001 |
| WO | 02/53155 | 7/2002 |
| WO | 02/81453 | 10/2002 |
| WO | 03/29245 | 4/2003 |
| WO | 03/32994 A2 | 4/2003 |
| WO | 03/57220 | 7/2003 |
| WO | 03/93243 | 11/2003 |
| WO | 03/96980 | 11/2003 |
| WO | 2004/022572 A1 | 3/2004 |
| WO | 2004/030633 A2 | 4/2004 |
| WO | 2004/031160 A2 | 4/2004 |
| WO | 2004/070050 A2 | 8/2004 |
| WO | 2004/111031 A1 | 12/2004 |
| WO | 2005/042488 A1 | 5/2005 |
| WO | 2005/059109 A2 | 6/2005 |
| WO | 2005/060661 A2 | 7/2005 |
| WO | 2005/089752 A2 | 9/2005 |
| WO | 2005/099693 A2 | 10/2005 |
| WO | 2006/010642 A1 | 2/2006 |
| WO | 2006/027266 A1 | 3/2006 |
| WO | 2006/028226 A1 | 3/2006 |
| WO | 2006/124118 A1 | 11/2006 |
| WO | 2007/012661 A1 | 2/2007 |

(56) References Cited

FOREIGN PATENT DOCUMENTS

| | | |
|---|---|---|
| WO | 2007/045877 A1 | 4/2007 |
| WO | 2007/126765 A2 | 11/2007 |
| WO | 2007/127010 A2 | 11/2007 |
| WO | 2008/034909 A2 | 3/2008 |
| WO | 2008/119015 A2 | 10/2008 |
| WO | 2009/055053 A2 | 4/2009 |
| WO | 2009/061587 A1 | 5/2009 |
| WO | 2010/099238 A1 | 9/2010 |
| WO | 2011/103202 A2 | 8/2011 |
| WO | 2011/106570 A1 | 9/2011 |
| WO | 2012/018948 A2 | 2/2012 |
| WO | 2012/142208 A1 | 10/2012 |
| WO | 2012/145330 A1 | 10/2012 |
| WO | 2012/158884 A1 | 11/2012 |
| WO | 2013/066440 A1 | 5/2013 |
| WO | 2013/079964 A1 | 6/2013 |
| WO | 2013/152342 A1 | 10/2013 |
| WO | 2013/153342 A1 | 10/2013 |
| WO | 2013/184681 A1 | 12/2013 |
| WO | 20141043208 A1 | 3/2014 |
| WO | 2014/052237 A1 | 4/2014 |
| WO | 20141113260 A1 | 7/2014 |
| WO | 20161090098 A1 | 6/2016 |
| WO | 20161090101 A1 | 6/2016 |
| WO | 20161090105 A1 | 6/2016 |

OTHER PUBLICATIONS

Cinar et al. Androgen Receptor Mediates the Reduced Tumor Growth, Enhanced Androgen Responsiveness, and Selected Target Gene Transactivation in Human Prostate Cancer Cell Line. Cancer Research. 2001. v. 61. pp. 7310-7317.

Chobanian et al., A facile microwave-assisted palladium-catalyzed cyanation of aryl chlorides. Tetrahed Lett. May 8, 2006;47(19):3303-5.

Chen et al., Molecular determinants of resistance to antiandrogen therapy. Nat Med. Jan. 2004;10(1):33-9. Epub Dec. 21, 2003.

Chang et al., "Molecular Cloning of Human and Rat Complementary DNA Encoding Androgen Receptors", Science, 1988, 240, 324-326.

Castration-Resistant Prostate Cancer, American Urological Association, www.auanet.org/education/guidelines/castration-resistant-prostate-cancer.- cfm, 2015, 21 pages.

Carver et al., "Reciprocal Feedback Regulation of PI3K and Androgen Receptor Signaling in PTEN-Deficient Prostate Cancer", Cancer Cell., 2011, 19, 575-586.

Cai et al., "c-Jun Has Multiple Enhancing Activities in the Novel Cross Talk Between the Androgen Receptor and ETS Variant Gene 1 in Prostate Cancer", Mol. Cancer Res, 2007, 5(7), 725-735.

Butler, "Mammalian Cell Biotechnology: A Practical Approach", 1991, 6 pages.

Burnstein et al. Androgen Glucocorticoid Regulation of Androgen Receptor cDNA Expression. Molecular and Cellular Endocrinology. 1995. v. 115, pp. 177-186.

Bundgaard, "Design of Application of Prodrugs", Harwood Academic Publishers, 1991, Chapter 5, 113-191.

Brockschmidt et al., "The Two Most Common Alleles of the Coding GGN Repeat in the Androgen Receptor Gene Cause Differences in Protein Function", J. Mol. Endocrinol., 2007, 39, 1-8.

Bredenberg, S. et al. (Jan. 1, 2003). "New Concepts in Administration of Drugs in Tablet Form," Comprehensive Summaries of Uppsala Dissertations from the Faculty of Pharmacy ACTA Universitatis Upsaliensis Uppsala, 83 pages.

Bohl et al., "Structural Basis for Antagonism and Resistance of Bicalutamide in Prostate Cancer", Proc. Nat. Acad. Sci, 2005, 102(17), 6201-6206.

Body, "Prevention and treatment of side-effects of systemic treatment: bone loss", Annals of Oncology, 2010, vol. 21, Supplement 7, vii180-vii185.

Batch et al., "Androgen Receptor Gene Mutations Identified by SSCP in Fourteen Subjects with Androgen Insensitivity Syndrome", Hum. Mol Genet., 1992, 1(7), 497-503.

Balk, "Androgen Receptor as a Target in Androgen-Independent Prostate Cancer", Urology, 2002, 60(3A), 132-138.

Balbas Minna D et al: "Overcoming mutation-based resistance to antiandrogens with rational drug design", E-Life, vol. 2, pp. e00499/1-21, XP009173001.

Baek et al., "Exchange of N-CoR Corepressor and Tip60 Coactivator Complexes Links Gene Expression by NF-kappaB and Beta-Amyloid Precursor Protein", Cell, 2002, 110, 55-67.

Ausubel et al., "Current Protocols in Molecular Biology", Wiley Interscience Publishers, 1995, 2, 18 pages.

Auricchio et al., "VAL 201—An Inhibitor of Androgen Receptor-associated Src and a Potential Treatment of Castration-resistant Prostate Cancer", European Oncology & Hematology, 2012, vol. 8, No. 1, 32-35.

Anonymous: "NCT01946204 on Sep. 18, 2013: A Study of ARN-509 in Men With Non-Metastatic Castration-Resistant Prostate Cancer", ClinicalTrials.gov Archive, Sep. 18, 2013 (Sep. 18, 2013), pp. 1-4, XP55251019, Retrieved from the Internet: URL:https://clinicaltrials.gov/archive/NCT01946204/2013_09_ 18 [retrieved on Feb. 17, 2016].

Amaral et al., "Castration-Resistant Prostate Cancer: Mechanisms, Targets, and Treatment", Hindawi Publishing Corporation, Prostate Cancer, Epub Mar. 5, 2012, vol. 2012, Article ID 327253, 11 pages.

Alva et al., "I. Phase II study of Cilengitide (EMD 121974, NSC 707544) in Patients with Non-Metastatic Castration Resistant Prostate Cancer, NCI-6735. A study by the DOD/PCF Prostate Cancer Clinical Trials Consortium", Investigational New Drugs, 2012, 30(2), 749-757.

A Textbook of Drug Design and Development, P. Krogsgaard-Larson and H. Bundgaard, eds. Ch 5, pp. 113-191 (Harwood Academic Publishers, 1991).

"Hormonal Treatments for Uterine Fibroids", Hormone Therapy for Fibroids, http://www.uterine-fibroids.org/HormonalTreatments.html, 2010, 2 pages.

"FDA ODAC Briefing Statement: Issues Concerning the Development of Products for the Treatment of Patients with Non-Metastatic Castration-Resistant Prostate Cancer", Sep. 14, 2011, 9 pages.

"Fact Sheet-Prostrate-Specific Antigen (PSA) Test", 2014, National Cancer Institute, 6 pages.

"Classification of Powders", The Pharmaceutics and Compounding Laboratory, http://pharmlabs.unc.edu/labs/powders/classification.htm, accessed Aug. 9, 2016, 2 pages.

"ARN-509 Update: Phase I Study-Prostrate Cancer", HealingWell.com, 2014, 3 pages.

Kingsman et al., "Replication in Saccharomyces cerevisiae of Plasmid pBR313 Carrying DNA from the Yeast trpl Region", Gene, 1979, 7, 141-152.

Keown et al., "Methods for Introducing DNA Into Mammalian Cells", Methods in Enzymology, 1990, 185, 527-537.

Kemppainen et al., "Distinguishing Androgen Receptor Agonists and Antagonists: Distinct Mechanisms of Activation by Medroxyprogesterone Acetate and Dihydrotestosterone", Mol. Endocrinol., 1999, 13, 440-454.

Kawai et al., "Site-Specific Fluorescent Labeling of Rna Molecules by Specific Transcription Using Unnatural Base Pairs", J. Am Chem. Soc., 2005, 127(49), 17286-17295.

Kato et al., "Activation of the Estrogen Receptor through Phosphorylation by Mitogenactivated Protein Kinase", Science, 1995, 270, 1491-1494.

Karvonen et al., "Interaction of Androgen Receptors with Androgen Response Element in Intact Cells", The Journal of Biological Chemistry, 1997, 272(25), 15973-15979.

Karp et al., "Prostate Cancer Prevention: Investigational Approaches and Opportunities", Cancer Res., v. 56 (Dec. 15, 1996) pp. 5547-5556.

Kagabu, "Methyl, Trifluoromethyl, and Methoxycarbonyl-Introduction to the Fifth Position on the Pyridine Ring of Chloronicotinyl Insecticide Imidacloprid", Synth Comm. 2006, 36(9), 1235-1245.

Jung et al., Structure-activity relationship for thiohydantoin androgen receptor antagonists for castration-resistant prostate cancer

(56) References Cited

OTHER PUBLICATIONS (CRPC). J Med Chem. Apr. 8, 2010;53(7):2779-96. doi: 10.1021/jm901488g. Epub Sep. 27, 2011. 59 pages.
Jones, "Proteinase Mutants of *Saccharomyces cerevisae*", Genetics, 1977, 85, 23-33.
Johnson et al., "Relationships between drug activity in NCI preclinical in vitro and in vivo models and early clinical trials", British Journal of Cancer, 2001, 84(10), 1424-1431.
J. Holzbeierlein et al., "Gene Expression Analysis of Human Prostate Carcinoma during Hormonal Therapy Identifies Androgen-Responsive Genes and Mechanisms of Therapy Resistance", Am. J. Pathology, vol. 164, No. 1 (Jan. 2004) pp. 217-227.
Hwang et al., "Angiogenesis inhibitors in the treatment of prostate cancer", Journal of Hematology & Oncology, 2010, vol. 3, No. 26, 1-12.
Huang et al., "AR Possess an Intrinsic Hormone-Independent Transcriptional Activity", Mol Endocrinol., 2002, 16(5), 924-937.
Horoszewicz et al., "LNCaP Model of Human Prostatic Carcinoma", Cancer Res., 1983, 43, 1809-1818.
Hong et al., "Non Metastatic Castration-Resistant Prostate Cancer", Korean Journal of Urology, 2014, 55, 153-160.
Homma et al., "Differential Levels of Human Leukocyte Antigen-Class I, Multidrugresistance 1 and Androgen Receptor Expressions in Untreated Prostate Cancer Cells: The Robustness of Prostate Cancer", Oncol. Rep., 2007, 18, 343-346.
Holzbeierlein et al., "Gene Expression Analysis of Human Prostate Carcinoma During Hormonal Therapy Identifies Androgen-Responsive Genes and Mechanisms of Therapy Resistance", Am. J. Pathology, 2004, 164(1), 217-227.
Higuchi et al., "Pro-Drugs as Novel Delivery Systems", 1975, vol. 14 of the A.C.S. Symposium Series, 6 pages.
Heath Elisabeth I et al: "A phase I dose-escalation study of oral BR-DIM (BioResponse 3,3 '-Diindolylmethane) in castrate-resistant, non-metastatic prostate cancer", American Journal of Translational Research, vol. 2, No. 4, 2010, pp. 402-411.
Hamilton-Reeves et al, "Isoflavone-Rich Soy Protein Isolate Suppresses Androgen Receptor Expression Without Altering Estrogen Receptor-Beta Expression or Serum Hormonal Profiles in Men at High Risk of Prostate Cancer", J. Nutr., 2007, 137, 1769-1775.
Gura, "Cancer Models: Systems for Identifying New Drugs Are Often Faulty", Science, Nov. 1997, vol. 278, No. 5340, 1041-1042.
Gregory et al., "Androgen Receptor Stabilization in Recurrent Prostate Cancer is Associated with Hypersensitivity to Low Androgen", Cancer Res, 2001, 61, 2892-2898.
Gregory et al., "A Mechanism for Androgen Receptor-Mediated Prostate Cancer Recurrence After Androgen Deprivation Therapy", Cancer Res., 2001, 61, 4315-4319.
Graham et al., "A New Technique for the Assay of Infectivity of Human Adenovirus 5 DNA", Virology, 1973, 52, 456-467.
Grad et al., "Multiple Androgen Response Elements and a Myc Consensus Site in the Androgen Receptor (AR) Coding Region are Involved in Androgen-Mediated Up-Regulation of AR Messenger RNA", Mol Endocrinol, 1999, 13, 1896-1911.
Goubet et al., "Conversion of a Thiohydantoin to the Corresponding Hydantoin via a Ring-Opening/Ring Closure Mechanism", Tetrahedron Letters, 1996, 37(43), 7727-7730.
Gomella, "Effective testosterone suppression for prostate cancer: is there a best castration therapy?", Rev. Urol., 2009, vol. 11, No. 2, 52-60.
Golub et al., "Molecular Classification of Cancer: Class Discovery and Class Prediction by Gene Expression Monitoring", Science, Oct. 1999, vol. 286, 531-537.
Godbole et al., "New Insights into the Androgen-Targeted Therapies and Epigenetic Therapies in Prostate Cancer", Prostate Cancer, 2011, 1-13.
Glass et al., "The Coregulator Exchange on Transcriptional Functions of Nuclear Receptors", Genes Dev., 2000, 14, 121-141.
Gioeli et al., "Androgen Receptor Phosphorylation Regulation and Identification of the Phosphorylation Sites", J Biol Chem, 2002, 277(32), 29304-29314.
Genentech, Oct. 2011, A Phase I, Open-Label Study of the Safety and Pharmacokinetics of Escalating Doses of DSTP 3086S in Patients with Metastatic Castration-Resistant Prostate Cancer, 2 pages.
Gelmann, "Molecular Biology of the Androgen Receptor", J. Clin. Oncol., 2002, 20, 3001-3015.
Foury et al., "Control of the Proliferation of Prostate Cancer Cells by an Androgen and Two Antiandrogens. Cell Specific Sets of Responses", J. Steroid Biochem. Molec. Bioi., 1998, 66(4), 235-240.
Font de Mora et al., "AIB1 is a Conduit for Kinase-Mediated Growth Factor Signaling to the Estrogen Receptor", Mol. Cell. Biol., 2000, 20(14), 5041-5047.
Foks et al., "Synthesis, Fungicidal and Antibacterial Activity of New Pyridazine Derivatives", Heterocycles, 2009, 78(4), 961-975.
Feldman et al., "The Development of Androgen-Independent Prostate Cancer", Nature Reviews Cancer, 2001, 1, 34-45.
Feher et al., "BHB: A Simple Knowledge-Based Scoring Function to Improve the C95 Efficiency of Database Screening", J. Chem. Inf. Comput. Sci., 2003, 43(4), 1316-1327.
Elokdah et al., "Design, Synthesis, and Biological Evaluation of Thia-Containing Compounds with Serum HDL-Cholesterol-Elevating Properties", J. Med. Chem., 2004, 47(3), 681-695.
Ellwood-Yen et al., "Myc-Driven Murine Prostate Cancer Shares Molecular Features with Human Prostate Tumors", Cancer Cell, 2003, 4(3), 223-238.
Ellis et al., "Characterization of a Novel Androgen-Sensitive, Prostate-Specific Antigen-Producing Prostatic Carcinoma Xenograft: LuCaP 23", Clin Cancer Res, 1996, 2, 1039-1048.
Edwards et al., "Androgen Receptor Gene Amplification and Protein Expression in Hormone Refractory Prostate Cancer", British Journal of Cancer, 2003, 89, 552-556.
Dhal et al., "Synthesis of Thiohydantoins, Thiazolidones and their Derivatives from N1-(4'-aryl thiazole 2'-YL) Thioureas", J. Indian Chem. Soc., 1973, 50(1), 680-684.
Design of Prodrugs, edited by H. Bundgaard, (Elsevier, 1985).
DePrimo et al. "Transcriptional Programs Activated by Exposure of Human Prostate Cancer Cells to Androgen", Genome Biology, 2002, 3(7), 1-12.
Depalo et al., "GnRH agonist versus GnRH antagonist in in vitro fertilization and embryo transfer (IVF/ET)", Reproductive Biology and Endocrinology, 2012, 10, 26-33.
Craft et al., "Evidence for Clonal Outgrowth of Androgen-Independent Prostate Cancer Cells from Androgen-Dependent Tumors Through a Two-Step Process", Cancer Res, 1999, 59,5030-5036.
Craft et al., "A Mechanism for Hormone-Independent Prostate Cancer Through Modulation of Androgen Receptor Signaling by the HER-2/Neu Tyrosine Kinase", Nature Medicine, 1999, 5(3), 280-285.
Cousty-Berlin, et al., "Preliminary Pharmacokinetics and Metabolism of Novel Non-steroidal Antiandrogens in the Rat: Relation of their Systemic Activity to the Formation of a Common Metabolite", J. Steroid Biochem. Molecular Bio., 1994, 51(1/2), 47-55.
Iran Chris et al: "Development of a Second-Generation Antiandrogen for Treatment of Advanced Prostate Cancer", Science (Washington D C), vol. 324, No. 5928, May 2009 (May 2009), pp. 787-790.
Smith et al: "ARN-509 in Men With High Risk Nonmetastatic Castration-Resistant Prostate Cancer", Annals of Oncology; Abstract Book of the 37th Esmo Congress, Kluwer, Dordrecht, NL; Vienna, Austria, vol. 23, No. Suppl. 9, Sep. 17, 2012 (Sep. 17, 2012), p. 303.
Matthew R. Smith et al: "Apalutamide Treatment and Metastasis-free Survival in Prostate Cancer", The New England Journal of Medicine,—Nejm—, vol. 378, No. 15, Apr. 12, 2018, pp. 1408-1418.
Sambrook et al., "Molecular Cloning: A Laboratory Manual", 2.sup.nd Edition, Table of Contents, Cold Spring Harbor Laboratory Press, Cold Spring Harbor, 1989, 30 pages.
Sack et al., "Crystallographic Structures of the Ligand-Binding Domains of the Androgen Receptor and its T877A Mutant Complexed with the Natural Agonist Dihydrotestosterone", Proc Natl Acad Sci, 2001, 98(9), 4904-4909.

(56) References Cited

OTHER PUBLICATIONS

Ryan et al., "Abiraterone in Metastatic Prostate Cancer without Previous Chemotherapy", New England Journal of Medicine, Jan. 10, 2013, vol. 368, No. 2, 138-148.
Rooseboom et al., "Enzyme-Catalyzed Activation of Anticancer Prodrugs", Pharmacological Reviews, 2004, 56, 53-102.
Remington: Practice of the Science and Pharmacy, 19th Edition, Table of Contents, Gennaro (ed.), 1995, Mack Publishing Company, Easton, PA, 5 pages.
Reagan-Shaw S et al: "Dose translation from animal to human studies revisited", FASEB Journal, FED. of American Soc. for Experimental Biology, US, vol. 22, Jan. 1, 2007 (Jan. 1, 2007), pp. 659-661.
Rathkopf et al., "A phase I study of the androgen signaling inhibitor ARN-509 in patients with metastatic castration-resistant prostate cancer (mCRPC)", J. Clin. Oncol. 30, Suppl. Abstr, 4548, May 30, 2012.
Rathkopf et al., "A First-In-Human. Open-Label. Phase 1/11 Safety. Pharmacokinetic and Proof-of-Concept Study of ARN—509 in Patients with Progressive Advanced Castration—Resistant Prostate Cancer (CRPC )", J. of Clin. Oncol.; ASCO Annual Meeting, 2011, 29(15), 2 pages.
Rathkopf Dana E et al: "Phase I study of ARN-509, a novel antiandrogen, in the treatment of castration-resistant prostate cancer", J Clin Onc,vol. 31 (28), Oct. 1, 2013, pp. 3525-3530, XP008166079.
Rathkopf Dana E (Correspondence) et al: "Phase I/II safety and pharmacokinetic (PK) study of ARN—509 in patients with metastatic castration—resistant prostate cancer (mCRPC): Phase I results of a Prostate Cancer Clinical Trials Consortium study", Journal of Clinical Oncology, American Society of Clinical Oncology, US vol. 30, No. 5, Suppl. 1 Feb. 10, 2012 (Feb. 10, 2012).
Rathkopf Dana E (Correspondence) et al: "A phase II study of the androgen signaling inhibitor ARN—509 in patients with castration—resistant prostate cancer (CRPC)", Journal of Clinical Oncology; 2012 Annual Meeting of the American Society of Clinical Oncology, ASCO, American Society of Clinical Oncology, US; Chicago, IL, United States, vol. 30, No. 15, Suppl. 1, May 20, 2012 (May 20, 2012).
Raffo et al., "Overexpression of bcl-2 Protects Prostate Cancer Cells from Apoptosis in Vitro and Confers Resistance to Androgen Depletion in Vivo", Cancer Research, 1995, 55, 4438-4445.
Presentation of Charles Sawyers, Prostate Cancer Foundation Scientific Retreat, Scottsdale, Arizona, Sep. 29-Oct. 1, 2005.
Perou et al., "Molecular Portraits of Human Breast Tumors", Nature, 2000, 406, 747-752.
P.J. Creaven et al., "Pharmacokinetics and Metabolism of Nilutamide", Supp. Urology, vol. 37, No. 2 (Feb. 1991) pp. 13-19.
Ouk et al., "Development of Androgen Receptor Inhibitors for Hormone-Refractory Prostate Cancer", Prostate Cancer Foundation Meeting, Scottsdale, AZ, Sep. 29-Oct. 1, 2005, 1 page.
Ouaissi et al., "Rationale for Possible Targeting of Histone Deacetylase Signaling in Cancer Diseases with a Special Reference to Pancreatic Cancer", Journal of Biomedicine and Biotechnology, 2011, 8 pages.
Osanto et al., "Emerging novel therapies for advanced prostate cancer", Therapeutic Advances in Urology, 2012, vol. 4, No. 1, 3-12.
Norris et al. "Peptide Antagonists of the Human Estrogen Receptor", Science, 1999, 285, 744-746.
NCBI, "Definition: *Homo sapiens* Androgen", Nucleotide, 2007, 7 pages. NM.sub.-000044<http://www.ncbi.nlm.nih.gov:80/entrez/viewer.fcgi?cmd=- Retrieve&db=nucleotide&list.sub.- uids= 21322251 &dopt=Gen Ban k&term=sapiens+AR+androgen+receptor+prostate+cancer&qty= 1>gi:21322251.
Navone et al., "Model Systems of Prostate Cancer: Uses and Limitations", Cancer Metastasis, 1999, 17, 361-371.
Nam et al., "Action of the Src Family Kinase Inhibitor, Dasatinib (BMS-354825), on Human Prostate Cancer Cells", Cancer Res., 2005, 65(20), 9185-9189.
Naik et al., "Synthesis, Spectroscopic and Thermal Studies of Bivalent Transition Metal Complexes with the Hydrazone Derived from 2-Benzimidazolyl Mercaptoaceto Hydrazile and o-Hydroxy Aromatic Aldehyde", Indian Journal of Chemistry, 2008, 1793-1797.
Muller et al., "BCR First Exon Sequences Specifically Activate the BCRIABL Tyrosine Kinase Oncogene of Philadelphia ChromosomePositive Human Leukemias", Mol. & Cell, Biol., 1991, 11(4), 1785-1792.
Mulholland et al., "Cell Autonomous Role of PTEN in Regulating Castration-Resistant Prostate Cancer Growth", Cancer Cell., 2011, 19, 792-804.
Morgan et al., "(RAD001 (Everolimus) Inhibits Growth of Prostate Cancer in the Bone and the Inhibitory Effects Are Increased by Combination With Doxetaxel and Zoledronic Acid", The Prostate, Jun. 1, 2008, 861-871.
Millennium-Takeda, "Press Release: Clinical Data Presented on Orteronel (TAK-700) Without Steroids in Non-Metastatic Prostate Cancer", 2012, 2 pages.
Migliaccio et al., "Steroid-Induced Androgen Receptor-Oestradiol Receptor beta-SRC Complex Triggers Prostate Cancer Cell Proliferation", Embo J, 2000, 19(20), 5406-5417.
McDonnell et al., "Expression of the Protooncogene bcl-2 in the Prostate and its Association with Emergence of Androgen-Independent Prostate Cancer", Cancer Res, 1992, 52, 6940-6944.
Matias et al., "Structural Evidence for Ligand Specificity in the Binding Domain of the Human Androgen Receptor: Implications for Pathogenic Gene Mutations", J Biol Chem, 2000, 275(34), 26164-26171.
Matias et al., "Structural Basis for the Glucocorticoid Response in a Mutant Human Androgen Receptor (AR(ccr)) Derived from an Androgen-Independent Prostate Cancer", J Med Chem, 2002, 45, 1439-1446.
Matias et al., "Local Inhibition of Sebaceous Gland Growth by Topically Applied RU 58841", NY Acad. Sci., 1995, 761, 56-65.
Masiello et al., "Bicalutamide Functions as an Androgen Receptor Antagonist by Assembly of a Transcriptionally Inactive Receptor", J Biol Chem, 2002, 277(29), 26321-26326.
Marhefka et al., "Homology Modeling Using Multiple Molecular Dynamics Simulations and Docking Studies of the Human Androgen Receptor Ligand Binding Domain Bound to Testosterone and Nonsteroidal Ligands", J. Med. Chem., 2001, 44(11), 1729-1740.
Mansour et al., "Disruption of the Proto-Oncogene int-2 in Mouse Embryo-Derived Stem Cells: A General Strategy for Targeting Mutations to Non-Selectable Genes", Nature, 1988, 336, 348-352.
Manolagas et al., "Sex Steroids and Bone", Recent Prog Harm Res, 2002, 57, 385-409.
Lu et al. "Molecular Mechanisms of Androgen-Independent Growth of Human Prostate Cancer LNCaP-Al Cells", Endocrinology 1999, vol. 140, No. 11, pp. 5054-5059.
Lodish et al., "Endocrine side effects of broad-acting kinase inhibitors", Endocrine-Related Cancer, 2010, 17, R233-R244.
Lodde, Michele, et al,, Urology 76 (5), 2010, pp. 1189-1193.
Lobaccaro et al., "Molecular Modeling and in Vitro Investigations of the Human Androgen Receptor DNA-Binding Domain: Application for the Study of Two Mutations", Mol. Cell. Endocrinol., 1996, 116, 137-147.
Liu et al: "Lineage relationship between LNCaP and LNCaP-derived prostate cancer cell lines", Prostate, vol. 60, No. 2, Jan. 1, 2004 (Jan. 1, 2004), pp. 98-108.
Linja et al., "Amplification and Overexpression of Androgen Receptor Gene in Hormone-Refractory Prostate Cancer", Cancer Research, 2001, 61, 3550-3555.
Li et al., "Heterogeneous Expression and Functions of Androgen Receptor Co-Factors in Primary Prostate Cancer", Am J Pathol, 2002, 161(4), 1467-1474.
LeRoith et al., "The insulin-like growth factor system and cancer", Cancer Letters, 2003, 195, 127-137.
Laitinen et al., "Chromosomal Aberrations in Prostate Cancer Xenografts Detected by Comparative Genomic Hybridization", Genes Chromosomes Cancer, 2002, 35, 66-73.
Kuethe et al., "Synthesis of Disubstituted Imidazo[4,5-b]pyridin-2-ones", J. Org. Chem., 2004, 29, 69(22), 7752-7754.

(56) References Cited

OTHER PUBLICATIONS

Kousteni et al., "Nongenotropic, Sex-Nonspecific Signaling through the Estrogen or Androgen Receptors: Dissociation from Transcriptional Activity", Cell, 2001, 104, 719-730.
Kliment Jan: "Re: Salvage Therapy With Bicalutamide 150 mg in Nonmetastatic Castration-resistant Prostate Cancer", European Urology, vol. 59, No. 6, Jun. 2011 (Jun. 2011), pp. 1066-1067.
Klein et al., "Progression of Metastatic Human Prostate Cancer to Androgen Independence in Immunodeficient SCID Mice", Nat Med, 1997, 3(4), 402-408.
Kinoshita et al., "Methylation of the Androgen Receptor Minimal Promoter Silences Transcription in Human Prostate Cancer", Cancer Res, 2000, 60, 3623-3630.
Vogelzang et al., Urology, 1995; 46:220-226 (Year: 1995).
Scher et al., Lancet, 2010, 375(9724), 1437-1446.
Okegawa et al., International Journal of Urology, 2010; 17:950-955 (Year: 2010).
Molina et al., Phase I study of apalutamide (ARN) plus abiraterone acetate (AA), docetaxel (D) in patients (pts) with metastatic castrate-resistant prostate cancer (mCRPC), Annals of Oncology, vol. 28, Supplement 5, Abstract No. 837TiP, Sep. 2017.
Matsubara, et al., "Phase 1 study of darolutamide (ODM-201): a new-generation androgen receptor antagonist, in Japanese patients with metastatic castration-resistant prostate cancer"; Cancer Chemother Pharmacol, 2017, 80:1063-1072.
de Bono et al., "Abiraterone and Increased Survival in Metastatic Prostate Cancer", The New England Journal of Medicine, 2011, vol. 364, No. 21, pp. 1995-2005.
Chen, et al., Molecular determinants of resistance to antiandrogen therapy; Nature Medicine; vol. 10, No. 1, Jan. 2014; 33-39.
Zoppi et al., "Amino Acid Substitutions in the DNA-Binding Domain of the Human Androgen Receptor are a Frequent Cause of Receptor-Binding Positive Androgen Resistance", Mol. Endo., 1992, 6, 409-415.
Zhou et al., "A Ligand-Dependent Bipartite Nuclear Targeting Signal in the Human Androgen Receptor, Requirement for the DNA-Binding Domain and Modulation by NH2-Terminal and Carboxyl-Terminal Sequences", J Bio Chem, 1994, 269(18), 13115-13123.
Zhau, H.Y. et al. Androgen-repressed phenotype in human prostate cancer. Proc Natl Acad Sci U S A 93,15152-7 (1996).
Zarghami et al., "Steroid Hormone Regulation of Prostate-Specific Antigen Gene Expression in Breast Cancer", British Journal of Cancer, 1997, 75(4), 579-588.
Zakikhani et al., "Metformin is an AMP Kinase-Dependent Growth Inhibitor for Breast Cancer Cells", Cancer Res, 2006, 66(21), 10269-10273.
Yoshino et al., Design and synthesis of an androgen receptor pure antagonist (CH5137291) for the treatment of castration-resistant prostate cancer. Bioorg Med Chem. Dec. 1, 2010;18(23):8150-7. doi: 10.1016/j.bmc.2010.10.023. Epub Oct. 15, 2010.
Wooster et al., "A Germline Mutation in the Androgen Receptor Gene in Two Brothers with Breast Cancer and Reifenstein Syndrome", Nat. Genet., 1992, 2, 132-134.
Wermuth, "Molecular Variations Based on Isosteric Replacements", The Practice of Medicinal Chemistry, 1996, 13, 203-237.
Wermuth et al., "Designing Prodrugs and Bioprecursors, I: Carrier Prodrugs", The Pharmacological Basis of Therapeutics, The Practice of Medicinal Chemistry, Goodman and Gilman, eds., Macmillan Publishing Co., New York, Chapter 31, 1996, 28 pages.
Wang et al., "Prostate-Specific Deletion of the Murine Pten Tumor Suppressor Gene Leads to Metastatic Prostate Cancer", Cancer Cell, 2003, 4, 209-221.
Wang et al., "Overexpressed Androgen Receptor Linked to p21WAF1 Silencing May Be Responsible for Androgen Independence and Resistance to Apoptosis of a Prostate Cancer Cell Line", Cancer Research, 2001, 61(20), 7544-7551.
Wallen et al., "Androgen Receptor Gene Mutations in Hormone-Refractory Prostate Cancer", J. Pathology 1999, vol. 189, pp. 559-563.

Wainstein et al., "CWR22: Androgen-Dependent Xenograft Model Derived from a Primary Human Prostatic Carcinoma", Cancer Res, 1994, 54, 6049-6052.
Visakorpi et al., "In Vivo Amplification of the Androgen Receptor Gene and Progression of Human Prostate Cancer", Nat Genetics, 1995, 9, 401-406.
Veldscholte et al., "A Mutation in the Ligand Binding Domain of the Androgen Receptor of Human LNCaP Cells Affects Steroid Binding Characteristics and Response to Antiandrogens", Biochem Biophys Res Commun, 1990, 173, 534-540.
Van Dort et al., "Design, Synthesis, and Pharmacological Characterization of 4-[ 4,4-Dimethyl-3-(4-hydroxybutyl)-5-oxo-2-thioxo-1-imidazolidinyl]-2-iodobenzonitrile as a High-Affinity Nonsteroidal Androgen Receptor Ligand", J. Med. Chem., 2000, 43, 3344-3347.
Urlaub et al., "Isolation of Chinese Hamster Cell Mutants Deficient in Dihydrofolate Reductase Activity", Proc. Natl. Acad. Sci. USA, 1980, 77(7), 4216-4220.
U.S. Appl. Jung et al., filed Mar. 27, 2006., U.S. Appl. No. 60/785,978.
Tschumper et al., "Sequence of a Yeast DNA Fragment Containing a Chromosomal Replicator and the TRP1 Gene", Gene, 1980, 10, 157-166.
Tremblay et al., "Ligand-Independent Recruitment of SRC-1 to Estrogen Receptor Beta through Phosphorylation of Activation Function AF-1", Mol Cell, 1999, 3, 513-519.
Tran et al., "Development of a Second-Generation Antiandrogen for Treatment of Advanced Prostate Cancer", Science, 2009, 324(5928), 787-790.
Tombal, Annals of Oncology 23(suppl 10):x251-x258, 2012.
Teutsch et al., "Non-steroidal Antiandrogens: Synthesis and Biological Profile of High-affinity Ligands for the Androgen Receptor", J. Steroid Biochem. Mol. Biol., 1994, 48, 111-119.
Taplin et al., "Mutation of the Androgen-Receptor Gene in Metastatic Androgen Independent Prostate Cancer", N Engl J Med, 1995, 332(21), 1393-1398.
Taplin et al., "Androgen Receptor Mutations in Androgen-Independent Prostate Cancer: Cancer and Leukemia Group B Study 9663", J Clin Oncol, 2003, 21, 2673-2678.
Taplin et al. "Selection for Androgen Receptor Mutations in Prostate Cancers Treated with Androgen Antagonist", Cancer Res, 1999, 59, 2511-2555.
Takemoto et al., "Novel Pottasium Chanel Openers: Synthesis and Pharmacological Evaluation of New N-(substituted-3-pyridyl)-N'-alkylthioureas and Related Compounds", J Med. Chem., 1994, 37(1), 18-25.
Szelei et al. Androgen-Induced Inhibition of Proliferation in Human Breast Cancer MCF7 Cells Transfected with Androgen Receptor Endocrinology. 1997. v. 138 (4). pp. 1406-1412.
Sweet et al., "A Unique Point Mutation in the Androgen Receptor Gene in a Family with Complete Androgen Insensitivity Syndrome", Fertil. Steril., 1992, 58(4), 703-707.
Su et al., "Polymorphisms of Androgen Receptor Gene in Childhood and Adolescent Males with First-Onset Major Depressive Disorder and Association with Related Symptomatology", Int. J. Neurosci., 2007, 117, 903-917.
Stinchcomb et al., "Isolation and Characterisation of a Yeast Chromosomal Replicator", 1979, 282, 39-43.
Sperry et al., Androgen Binding Profiles of Two Distinct Nuclear Androgen Receptors in Atlantic Croaker (Micropogonias Undulates), Journal of Steroid Biochemistry & Molecular Biology, 2000, 73, 93-103.
Soto et al., "Control of Cell Proliferation: Evidence for Negative Control on C141 Estrogen-Sensitive T47D Human Breast Cancer Cells", Cancer Research, 1986, 46, 2271-2275.
Sonpavde, "Abiraterone acetate for metastatic prostate cancer" Lancet Oncology (2012), vol. 12, Issue 10, pp. 958-959.
Smith et al., "ARN-509 in Men with High Risk Non-Metastatic Castration-Resistant Prostate Cancer", European Journal of Cancer; European Cancer Congress, 2013, 49(2), 1 page.
Smith et al., "ARN-509 in Men with High Risk Non-Metastatic Castration-Resistant Prostate Cancer", Annals of Oncology, Abstract Book of the 37th ESMO Congress, Kluwer, Dordrecht, NL; Vienna, Austria, Sep. 1, 2012, vol. 23, No. Suppl. 9, p. 303.

(56) References Cited

OTHER PUBLICATIONS

Singh et al., "Androgen Receptor Antagonists (Antiandrogens): Structure-Activity Relationships", Current Medicinal Chemistry, 2000, 7, 211-247.

Simone, "Oncology: Introduction", Cecil Textbook of Medicine, 20th Edition, vol. 1, 1996, 1004-1010.

Shiau et al., "The Structural Basis of Estrogen Receptor/Coactivator Recognition and the Antagonism of this Interaction by Tamoxifen", Cell, 1998, 95, 927-937.

Shi et al., "Functional Analysis of 44 Mutant Androgen Receptors from Human Prostate Cancer", Can Res, 2002, 62(5), 1496-1502.

Sharifi et al., Advanced Drug Delivery Reviews, vol. 28, No. 1, 1997, pp. 121-138.

Shang, Y., Myers, M. & Brown, M. Formation of the androgen receptor transcription complex. Mol Cell 9, 601-10 (2002).

Shang et al., "Molecular Determinants for the Tissue Specificity of SERMs", Science, 2002, 295, 2465-2468.

Sderholm et al., "Three-Dimensional Structure-Activity Relationships of Nonsteroidal Ligands in Complex with Androgen Receptor Ligand-Binding Domain," J. Med. Chem., 2005, 48(4), 917-925.

Scher et al., "The Flutamide Withdrawal Syndrome: Its Impact on Clinical Trials in Hormone-Refractory Prostatic Cancer", J Clin Oncol 1993, 11, 1566-1572.

Scher et al., "Antitumour activity of MDV3100 in castration-resistant prostate cancer: a phase 1-2 study", Lancet, Apr. 24, 2010, 375(9724), 1437-1446.

Schellhammer et al., "Prostate Specific Antigen Decreases after Withdrawal of Antiandrogen Therapy with Bicalutamide or Flutamide in Patients Receiving Combined Androgen Blockade", J Urol, 1997, 157, 1731-1735.

Saunders et al., "Point Mutations Detected in the Androgen Receptor Gene of Three Men with Partial Androgen Insensitivity Syndrome", Clin. Endocrinol., 1992, 37, 214-220.

Sartor, Urology, 2003;61 (Supppl 2A): 25-31.

Sarker et al., "Targeting the PI3K/AKT Pathway for the Treatment of Prostate Cancer", Clinical Cancer Research, 2009, vol. 15, No. 15, 4799-4805.

Kapoor, et al., BMC Cancer; A phase II randomized placebo-controlled double-blind study of salvage radiation therap plus placebo versus SRT plus enzalutamide with high-risk PSA-recurrent prostate cancer after radical prostatectomy (SALV-ENZA); 2019; 10 pages.

Rathkopf, et al., "A phase I study of the androgen signaling inhibitor ARN- 509 in patients with metastatic castratio resistant prostate cancer (mCRPC)" Journal of Clinical Oncology (2012), vol. 30. suppl. 1.

Sartor; Progression of metastatic castrate-resistant prostate cancer: impact of therapeutic intervention in the post-docetaxel space Journal of Hematology & Oncology 2011, 4:18; 1-7.

Sauveur-Michel Maira et al., "Identification and characterization of NVP-BKM120, an orally available pan-class I PI3-kinase inhibitor", Molecular Cancer Therapeutics, vol. 11, No. 2, published on Dec. 21, 2011, pp. 317-328.

Vargas, et al., The Journal of Nuclear Medicine; Reproducibility and Repeatability of Semiquantitative 18 F-Fluorodihydrotestosterone Uptake Metrics in Castration-Resistant Prostate Cancer Metastases: A Prospective Multicenter Study; Oct. 2018; vol. 59, No. 10; pp. 1516-1523.

Al-Salama Zaina T: "Apalutamide: First Global Approval", Drugs, ADIS International Ltd, NZ, vol. 78, No. 6, Mar. 31, 2018 (Mar. 31, 2018), pp. 699-705, ISSN: 1179-1950, DOI: 10.1007/S40265-018-0900-Z.

Antonarakis, Eur Urol Rev., Management of metastatic castration-resistant prostate cancer, 2011 ; 6(2): 90-96.

FDA: "FDA approves new treatment for a certain type of prostate cancer using novel clinical trial endpoint", Feb. 14, 2018 (Feb. 14, 2018), Retrieved from the Internet: URL:https://www.fda.gov/newsevents/newsroom/pressannouncements/ucm596768.htm [retrieved on Jul. 12, 2018]; XP-002783009; 4 pages.

Fu, et al., Biochim Biophys Acta., Progress of molecular targeted therapies for prostate cancers, 2012; 1825(2): 140-152; 27 pages.

Geynisman Daniel M et al: "Second-generation Androgen Receptor-targeted Therapies in Nonmetastatic Castration-resistant Prostate Cancer: Effective Early Intervention or Intervening Too Early?", European Urology, Elsevier, Amsterdam, NL, vol. 70, No. 6, May 26, 2016 (May 26, 2016), pp. 971-973, ISSN: 0302-2838, DOI: 10.1016/J.EURURO.2016.05.026.

Hou, et al., Hindawi Publishing Corpration, Advances in Urology, Redefining Hormone Sensitive Disease in Advanced Prostate Cancer, vol. 2012, Article ID ID 978531, 6 pages.

Janssen Pharmaceutical Companies: "Erleada safety and efficacy. See full prescribing information for Erleada.", Retrieved from the Internet: URL:https://www.accessdata.fda.gov/drugsatfda _ docs/label/2018/21 0951 s000lbl.pdf, [retrieved on Feb. 5, 2020].

Janssen: "Submits New Drug Application to U.S. FDA for Apalutamide (ARN-509) to Treat Men with Non-Metastatic Castration-Resistant Prostate Cancer", Oct. 11, 2017 (Oct. 11, 2017) Retrieved from the Internet: URL:https://www.prnewswire.com/news-releases/janssen-submits-new-drug-application-to-usfda-for-apalutamide-arn-509-to-treat-men-with-non-metastatic-castration-resistant-prostatecancer-300534 704. html [retrieved on Jul. 12, 2018].

Kim, et al., Korean Journal of Urology, Current Treatment Strategies for Castration-Resistant Prostate Cancer, 2011, pp. 157-165.

Lonergan, et al., Journal of Carcinogenesis, Androgen receptor signaling in prostate cancer development and progression, 2011, 19 pages.

Nicholas et al., Urology, 1995, vol. 46, p. 220-226.

Penson et al: "Enzalutamide Versus Bicalutamide in Castration-Resistant Prostate Cancer: The Strive Trial",Journal of Clinical Oncology, vol. 34, No. 18, Jun. 20, 2016 (Jun. 20, 2016), pp. 2098-2106, US, ISSN: 0732-183X, DOI: 10.1200/JCO.2015.64.9285.

Riegman, et al., Molecular Endocrinology, The Promoter of the Prostate-Specific Antigen Gene Contains a Functional Androgen Responsive Element, 1991, pp. 1921-1930.

Shore et al.: "Novel Antiandrogen ARN-509 in High-Risk Nonmetastatic CastrationResistant Prostate Cancer", The Journal of Urology, vol. 193, No. 4S, May 19, 2015 (May 19, 2015).

Shore: "Darolutamide (ODM-201) for the treatment of prostate cancer", Expert Opinion on Pharmacotherapy, vol. 18, No. 9, Jun. 13, 2017 (Jun. 13, 2017), pp. 945-952, London, UK, ISSN: 1465-6566, DOI: 10.1080/14656566.2017.1329820.

Smith Matthew R et al: "Phase 2 Study of the Safety and Antitumor Activity of Apalutamide (ARN-509), a Potent Androgen Receptor Antagonist, in the High-risk Non metastatic Castrationresistant Prostate Cancer Cohort", European Urology, Elsevier, Amsterdam, NL, vol. 70, No. 6, May 6, 2016 (May 6, 2016), pp. 963-970, ISSN: 0302-2838, DOI: 10.1016/J.EURURO.2016.04.023.

Smith, et al., Ann. Oncol., Sep. 1, 2012, vol. 23, suppl. 9, p. ix303.

Wolf, et al, Molecular Endocrinology, Transcriptional Regulation of Prostate Kallikrein-Like Genes by Androgen, 1992, vol. 6, No. 5, pp. 753-762.

ANTI-ANDROGENS FOR THE TREATMENT OF NON-METASTATIC CASTRATE-RESISTANT PROSTATE CANCER

CROSS REFERENCE TO RELATED APPLICATIONS

This application is a continuation of U.S. patent application Ser. No. 15/851,444, filed Dec. 21, 2017, which is a continuation of U.S. patent application Ser. No. 14/034,460 filed Sep. 23, 2013, now U.S. Pat. No. 9,884,054, which claims priority to U.S. Patent Application Ser. No. 61/705,900, filed Sep. 26, 2012, the contents of which are incorporated by reference herein in its entirety for all purposes

FIELD OF THE INVENTION

Described herein are methods of treating non-metastatic castrate-resistant prostate cancer with anti-androgens, including but not limited to, 4-[7-(6-cyano-5-trifluoromethylpyridin-3-yl)-8-oxo-6-thioxo-5,7-diazaspiro[3.4]oct-5-yl]-2-fluoro-N-methylbenzamide.

BACKGROUND OF THE INVENTION

Prostate cancer is the second most frequently diagnosed cancer and the second leading cause of cancer death in males. The course of prostate cancer from diagnosis to death is best categorized as a series of clinical states based on the extent of disease, hormonal status, and absence or presence of detectable metastases: localized disease, rising levels of prostate-specific antigen (PSA) after radiation therapy or surgery with no detectable metastases, and clinical metastases in the non-castrate or castrate state.

SUMMARY OF THE INVENTION

In one aspect, described herein is a method of treating non-metastatic castration-resistant prostate cancer in a male human comprising administering a therapeutically effective amount of an anti-androgen to a male human with non-metastatic castration-resistant prostate cancer. In some embodiments, wherein the non-metastatic castration-resistant prostate cancer is high risk non-metastatic castration-resistant prostate cancer. In some embodiments, the male human with high risk non-metastatic castration-resistant prostate cancer has a prostate-specific antigen doubling time (PSADT) that is less than or equal to 10 months. In some embodiments, administration of the anti-androgen provides an increase in the metastasis-free survival of the male human.

In another aspect, described herein is a method of providing an increase in the metastasis-free survival of a male human with prostate cancer comprising administering a therapeutically effective amount of an anti-androgen to the male human with prostate cancer. In some embodiments, the prostate cancer is non-metastatic castration-resistant prostate cancer. In some embodiments, the prostate cancer is high risk non-metastatic castration-resistant prostate cancer. In some embodiments, the male human with high risk non-metastatic castration-resistant prostate cancer has a prostate-specific antigen doubling time (PSADT) that is less than or equal to 10 months.

In some embodiments, the anti-androgen is a non-steroidal anti-androgen.

In some embodiments, the anti-androgen binds directly to the ligand-binding domain of the androgen receptor.

In some embodiments, the anti-androgen is a second-generation anti-androgen.

In some embodiments, the anti-androgen is 4-[7-(6-cyano-5-trifluoromethylpyridin-3-yl)-8-oxo-6-thioxo-5,7-diazaspiro[3.4]oct-5-yl]-2-fluoro-N-methylbenzamide; 4-(3-(4-cyano-3-(trifluoromethyl)phenyl)-5,5-dimethyl-4-oxo-2-thioxoimidazolidin-1-yl)-2-fluoro-N-methylbenzamide (enzalutamide); or 4-[7-(4-cyano-3-trifluoromethylphenyl)-8-oxo-6-thioxo-5,7-diazaspiro[3.4]oct-5-yl]-2-fluoro-N-methylbenzamide (RD162).

In some embodiments, the anti-androgen is administered orally to the male human. In some embodiments, the anti-androgen is administered to the male human in the form of a tablet, a pill, a capsule, a solution, a suspension, or a dispersion. In some embodiments, the anti-androgen is administered to the male human on a continuous daily dosing schedule.

In some embodiments, the anti-androgen is 4-[7-(6-cyano-5-trifluoromethylpyridin-3-yl)-8-oxo-6-thioxo-5,7-diazaspiro[3.4]oct-5-yl]-2-fluoro-N-methylbenzamide. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered daily to the male human. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human at a dose of about 30 mg per day to about 480 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human at a dose of about 180 mg per day to about 480 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human at a dose of about 30 mg per day, about 60 mg per day, about 90 mg per day, about 120 mg per day, about 180 mg per day, about 240 mg per day, about 300 mg per day, about 390 mg per day, or about 480 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human at a dose of about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human on a continuous daily dosing schedule.

In any of the embodiments described herein, the methods of treatment further comprises administering a gonadotropin-releasing hormone (GnRH) agonist. In some embodiments, the GnRH agonist is leuprolide, buserelin, nafarelin, histrelin, goserelin, or deslorelin.

In any of the aforementioned aspects the effective amount of the anti-androgen is: (a) systemically administered to the male human; and/or (b) administered orally to the male human; and/or (c) intravenously administered to the male human; and/or (d) administered by injection to the male human.

In any of the aforementioned aspects, the effective amount of the anti-androgen is administered (i) once a day; or (ii) multiple times over the span of one day. In some embodiments, the effective amount of the anti-androgen is administered once a day, twice a day, three times a day or four times a day.

In any of the aforementioned aspects the effective amount of the anti-androgen is administered continuously or intermittently. In some embodiments, the effective amount of the anti-androgen is administered continuously. In some embodiments, the effective amount of the anti-androgen is administered daily.

In some embodiments, compounds provided herein are orally administered.

Other objects, features and advantages of the methods, uses and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description

DETAILED DESCRIPTION OF THE INVENTION

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, while an embodiment may be described as part of a series of steps or part of a more general structure, each said step may also be considered an independent embodiment in itself, combinable with others.

The transitional terms "comprising," "consisting essentially of," and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents), also provide, as embodiments, those which are independently described in terms of "consisting of" and "consisting essentially of."

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

Androgen receptor (AR) is a member of the steroid and nuclear receptor superfamily. Among this large family of proteins, only five vertebrate steroid receptors are known and include the androgen receptor, estrogen receptor, progesterone receptor, glucocorticoid receptor, and mineralocorticoid receptor. AR is a soluble protein that functions as an intracellular transcriptional factor. AR function is regulated by the binding of androgens, which initiates sequential conformational changes of the receptor that affect receptor-protein interactions and receptor-DNA interactions.

AR is mainly expressed in androgen target tissues, such as the prostate, skeletal muscle, liver, and central nervous system (CNS), with the highest expression level observed in the prostate, adrenal gland, and epididymis. AR can be activated by the binding of endogenous androgens, including testosterone and 5α-dihydrotestosterone (5α-DHT).

The androgen receptor (AR), located on Xq11-12, is a 110 kD nuclear receptor that, upon activation by androgens, mediates transcription of target genes that modulate growth and differentiation of prostate epithelial cells. Similar to the other steroid receptors, unbound AR is mainly located in the cytoplasm and associated with a complex of heat shock proteins (HSPs) through interactions with the ligand-binding domain. Upon agonist binding, AR goes through a series of conformational changes: the heat shock proteins dissociate from AR, and the transformed AR undergoes dimerization, phosphorylation, and translocation to the nucleus, which is mediated by the nuclear localization signal. Translocated receptor then binds to the androgen response element (ARE), which is characterized by the six-nucleotide half-site consensus sequence 5'-TGTTCT-3' spaced by three random nucleotides and is located in the promoter or enhancer region of AR gene targets. Recruitment of other transcription co-regulators (including co-activators and co-repressors) and transcriptional machinery further ensures the transactivation of AR-regulated gene expression. All of these processes are initiated by the ligand-induced conformational changes in the ligand-binding domain.

AR signaling is crucial for the development and maintenance of male reproductive organs including the prostate gland, as genetic males harboring loss of function AR mutations and mice engineered with AR defects do not develop prostates or prostate cancer. This dependence of prostate cells on AR signaling continues even upon neoplastic transformation. Androgen depletion (such as using GnRH agonists) continues to be the mainstay of prostate cancer treatment. However androgen depletion is usually effective for a limited duration and prostate cancer evolves to regain the ability to grow despite low levels of circulating androgens. Castration resistant prostate cancer (CRPC) is a lethal phenotype and almost all of patients will die from prostate cancer. Interestingly, while a small minority of CRPC does bypass the requirement for AR signaling, the vast majority of CRPC, though frequently termed "androgen independent prostate cancer" or "hormone refractory prostate cancer," retains its lineage dependence on AR signaling.

Prostate cancer is the second most common cause of cancer death in men in the US, and approximately one in every six American men will be diagnosed with the disease during his lifetime. Treatment aimed at eradicating the tumor is unsuccessful in 30% of men, who develop recurrent disease that is usually manifest first as a rise in plasma prostate-specific antigen (PSA) followed by spread to distant sites. Given that prostate cancer cells depend on androgen receptor (AR) for their proliferation and survival, these men are treated with agents that block production of testosterone (e.g. GnRH agonists), alone or in combination with anti-androgens (e.g. bicalutamide), which antagonize the effect of any residual testosterone on AR. The approach is effective as evidenced by a drop in PSA and regression of visible tumor (if present) in some patients; however, this is followed by regrowth as a castration resistant prostate cancer (CRPC) to which most patients eventually succumb. Recent studies on the molecular basis of CRPC have demonstrated that CRPC continues to depend on AR signaling and that a key mechanism of acquired resistance is an elevated level of AR protein (*Nat. Med,* 2004, 10, 33-39). AR targeting agents with activity in castration sensitive and castration resistant resistant prostate cancer have great promise in treating this lethal disease.

The course of prostate cancer from diagnosis to death is best categorized as a series of clinical states based on the extent of disease, hormonal status, and absence or presence of detectable metastases: localized disease, rising levels of prostate-specific antigen (PSA) after radiation therapy or surgery with no detectable metastases, and clinical metastases in the non-castrate or castrate state. Although surgery, radiation, or a combination of both can be curative for patients with localized disease, a significant proportion of these patients have recurrent disease as evidenced by a rising level of PSA, which can lead to the development of metastases, especially in the high risk group—a transition to the lethal phenotype of the disease.

Androgen depletion is the standard treatment with a generally predictable outcome: decline in PSA, a period of stability in which the tumor does not proliferate, followed by rising PSA and regrowth as castration-resistant disease. Molecular profiling studies of castration-resistance prostate cancers commonly show increased androgen receptor (AR) expression, which can occur through AR gene amplification or other mechanisms.

Anti-androgens are useful for the treatment of prostate cancer during its early stages. However, prostate cancer often advances to a 'hormone-refractory' state in which the disease progresses in the presence of continued androgen ablation or anti-androgen therapy. Instances of antiandrogen withdrawal syndrome have also been reported after prolonged treatment with anti-androgens. Antiandrogen withdrawal syndrome is commonly observed clinically and is defined in terms of the tumor regression or symptomatic relief observed upon cessation of antiandrogen therapy. AR mutations that result in receptor promiscuity and the ability of these anti-androgens to exhibit agonist activity might at least partially account for this phenomenon. For example, hydroxyflutamide and bicalutamide act as AR agonists in T877A and W741L/W741C AR mutants, respectively.

In the setting of prostate cancer cells that were rendered castration resistant via overexpression of AR, it has been demonstrated that certain anti-androgen compounds, such as bicalutamide, have a mixed antagonist/agonist profile (*Science,* 2009 May 8; 324(5928): 787-90). This agonist activity helps to explain a clinical observation, called the anti-androgen withdrawal syndrome, whereby about 30% of men who progress on AR antagonists experience a decrease in serum PSA when therapy is discontinued (*J Clin Oncol,* 1993. 11(8): p. 1566-72).

Prostate Cancer Stages

In the early stages of prostate cancer, the cancer is localized to the prostate. In these early stages, treatment typically involes either surgical removal of the prostate or radiation therapy to the prostate or observation only with no active intervention therapy in some patients. In the early stages where the prostate cancer is localized and requires intervention, surgery or radiation therapy are curative by eradicating the cancerous cells. About 30% of the time these procedures fail, and the prostate cancer continues to progress, as typically evidenced by a rising PSA level. Men whose prostate cancer has progressed following these early treatment strategies are said to have advanced or recurrent prostate cancer.

Because prostate cancer cells depend on the androgen receptor (AR) for their proliferation and survival, men with advanced prostate cancer are treated with agents that block the production of testosterone (eg, GnRH agonists), alone or in combination with anti-androgens (eg, bicalutamide), which antagonize the effect of any residual testosterone on AR. These treatments reduce serum testosterone to castrate levels, which generally slows disease progression for a period of time. The approach is effective as evidenced by a drop in PSA and the regression of visible tumors in some patients. Eventually, however, this is followed by regrowth referred to as castration-resistant prostate cancer (CRPC), to which most patients eventually succumb.

Castration-resistant prostate cancer (CRPC) is categorized as non-metastatic or metastatic, depending on whether or not the prostate cancer has metastasized to other parts of the body.

In some embodiments, prior to treatment with a second-generation anti-androgen men with non-metastatic CRPC are characterized as having the following:
1. Histologically or cytologically confirmed adenocarcinoma of the prostate without neuroendocrine differentiation or small cell features, with high risk for development of metastases.
2. Castration-resistant prostate cancer demonstrated during continuous androgen deprivation therapy (ADT)/post orchiectomy. For example defined as 3 consecutive rises of PSA, 1 week apart, resulting in two 50% increases over the nadir, with the last PSA >2 ng/mL.
3. Maintain castrate levels of testosterone (<50 ng/dL [1.72 nmol/L]) within 4 weeks of randomization and throughout the study.
4. Absence of distant metastasis by bone scan, CT or MRI scans.

Anti-Androgens

As used herein, the term "anti-androgen" refers to a group of hormone receptor antagonist compounds that are capable of preventing or inhibiting the biologic effects of androgens on normally responsive tissues in the body. In some embodiments, an anti-androgen is a small molecule. In some embodiments, an anti-androgen is an AR antagonist. In some embodiments, an anti-androgen is an AR full antagonist. In some embodiments, an anti-androgen is a first-generation anti-androgen. In some embodiments, an anti-androgen is a second-generation anti-androgen.

As used herein, the term "AR antagonist" or "AR inhibitor" are used interchangeably herein and refer to an agent that inhibits or reduces at least one activity of an AR polypeptide. Exemplary AR activities include, but are not limited to, co-activator binding, DNA binding, ligand binding, or nuclear translocation.

As used herein, a "full antagonist" refers to an antagonist which, at an effective concentration, essentially completely inhibits an activity of an AR polypeptide. As used herein, a "partial antagonist" refers an antagonist that is capable of partially inhibiting an activity of an AR polypeptide, but that, even at a highest concentration is not a full antagonist. By 'essentially completely' is meant at least about 80%, at least about 90%, at least about 95%, at least about 96%, at least about 97%, at least about 98% at least about 99%, or greater inhibition of the activity of an AR polypeptide.

As used herein, the term "first-generation anti-androgen" refers to an agent that exhibits antagonist activity of a wild-type AR polypeptide. However, first-generation anti-androgens differ from second-generation anti-androgens in that first-generation anti-androgens can potentially act as agonists in castration resistant prostate cancers (CRPC). Exemplary first-generation anti-androgens include, but are not limited to, flutamide, nilutamide and bicalutamide.

As used herein, the term "second-generation anti-androgen" refers to an agent that exhibits full antagonist activity of a wild-type AR polypeptide. Second-generation anti-androgens differ from first-generation anti-androgens in that second-generation anti-androgens act as full antagonists in cells expressing elevated levels of AR, such as for example, in castration resistant prostate cancers (CRPC). Exemplary second-generation anti-androgens include 4-[7-(6-cyano-5-trifluoromethylpyridin-3-yl)-8-oxo-6-thioxo-5,7-diazaspiro[3.4]oct-5-yl]-2-fluoro-N-methylbenzamide (also known as ARN-509; CAS No. 956104-40-8); 4-(3-(4-cyano-3-(trifluoromethyl)phenyl)-5,5-dimethyl-4-oxo-2-thioxoimidazolidin-1-yl)-2-fluoro-N-methylbenzamide (also known as MDV3100 or enzalutamide; CAS No: 915087-33-1) and 4-[7-(4-cyano-3-trifluoromethylphenyl)-8-oxo-6-thioxo-5,7-diazaspiro[3.4]oct-5-yl]-2-fluoro-N-methylbenzamide (RD162; CAS No. 915087-27-3). In some embodiments, a second-generation anti-androgen binds to an AR polypeptide at or near the ligand binding site of the AR polypeptide.

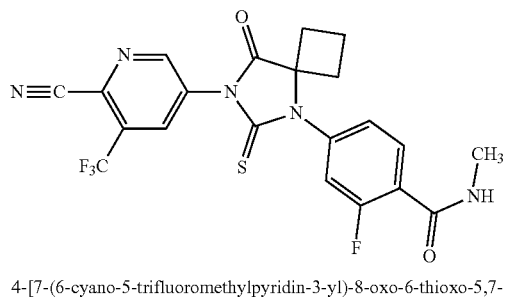

4-[7-(6-cyano-5-trifluoromethylpyridin-3-yl)-8-oxo-6-thioxo-5,7-diazaspiro[3.4]oct-5-yl]-2-fluoro-N-methylbenzamide (ARN-509)

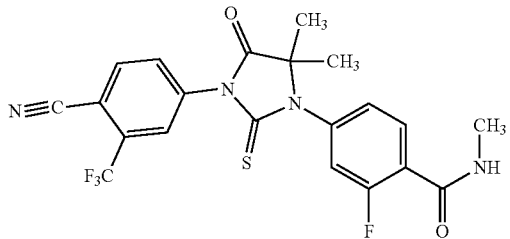

4-(3-(4-cyano-3-(trifluoromethyl)phenyl)-5,5-dimethyl-4-oxo-2-thioxoimidazolidin-1-yl)-2-fluoro-N-methylbenzamide (enzalutamide)

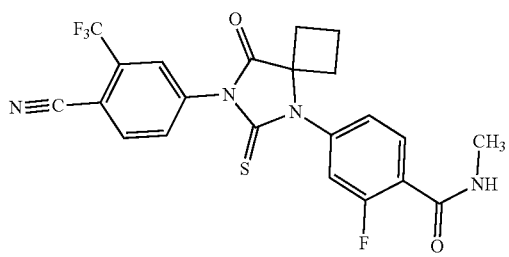

4-[7-(4-cyano-3-trifluoromethylphenyl)-8-oxo-6-thioxo-5,7-diazaspiro[3.4]oct-5-yl]-2-fluoro-N-methylbenzamide (RD162).

In some embodiments, an anti-androgen contemplated in the methods described herein inhibits AR nuclear translocation, DNA binding to androgen response elements, and coactivator recruitment. In some embodiments, an anti-androgen contemplated in the methods described herein exhibits no agonist activity in AR-overexpressing prostate cancer cells.

4-[7-(6-Cyano-5-trifluoromethylpyridin-3-yl)-8-oxo-6-thioxo-5,7-diazaspiro[3.4]oct-5-yl]-2-fluoro-N-methylbenzamide 4-[7-(6-Cyano-5-trifluoromethylpyridin-3-yl)-8-oxo-6-thioxo-5,7-diazaspiro[3.4]oct-5-yl]-2-fluoro-N-methylbenzamide is a second-generation anti-androgen that binds directly to the ligand-binding domain of AR, impairing nuclear translocation, AR binding to DNA and AR target gene modulation, thereby inhibiting tumor growth and promoting apoptosis. 4-[7-(6-Cyano-5-trifluoromethylpyridin-3-yl)-8-oxo-6-thioxo-5,7-diazaspiro[3.4]oct-5-yl]-2-fluoro-N-methylbenzamide binds AR with greater affinity than bicalutamide, and induces partial or complete tumor regression in non-castrate hormone-sensitive and bicalutamide-resistant human prostate cancer xenograft models (Clegg et al. Cancer Res Mar. 15, 2012 72; 1494). 4-[7-(6-Cyano-5-trifluoromethylpyridin-3-yl)-8-oxo-6-thioxo-5,7-diazaspiro[3.4]oct-5-yl]-2-fluoro-N-methylbenzamide lacks the partial agonist activity seen with bicalutamide in the context of AR overexpression.

Disclosed herein is the use of 4-[7-(6-Cyano-5-trifluoromethylpyridin-3-yl)-8-oxo-6-thioxo-5,7-diazaspiro[3.4]oct-5-yl]-2-fluoro-N-methylbenzamide in the treatment of non-metastatic castration-resistant prostate cancer in a male human.

Also described herein, is the use of a second-generation anti-androgen in the treatment of non-metastatic castration-resistant prostate cancer in a male human.

In a Phase II clinical trial of male humans with non-metastatic castration-resistant prostate cancer, oral administration of 240 mg of 4-[7-(6-cyano-5-trifluoromethylpyridin-3-yl)-8-oxo-6-thioxo-5,7-diazaspiro[3.4]oct-5-yl]-2-fluoro-N-methylbenzamide on a continuous daily dosing schedule resulted in a ≥50% decline in PSA from baseline at week 12 (i.e. about 3 months) in a portion of the patients. At 3 months, a PSA50 (i.e. ≥50% decline in PSA from baseline) and a PSA90 (i.e. ≥90% decline in PSA from baseline) were observed in 91% and 38% of the males that were orally administered 240 mg of 4-[7-(6-cyano-5-trifluoromethylpyridin-3-yl)-8-oxo-6-thioxo-5,7-diazaspiro[3.4]oct-5-yl]-2-fluoro-N-methylbenzamide on a continuous daily dosing schedule, respectively. At 6 months, a PSA50 and a PSA90 were observed in 91% and 55% of the males that were orally administered 240 mg of 4-[7-(6-cyano-5-trifluoromethylpyridin-3-yl)-8-oxo-6-thioxo-5,7-diazaspiro[3.4]oct-5-yl]-2-fluoro-N-methylbenzamide on a continuous daily dosing schedule, respectively.

Certain Terminology

Throughout this specification, words are to be afforded their normal meaning, as would be understood by those skilled in the relevant art. However, so as to avoid misunderstanding, the meanings of certain terms will be specifically defined or clarified.

The term "cancer" as used herein refers to an abnormal growth of cells which tend to proliferate in an uncontrolled way and, in some cases, to metastasize (spread).

The term "prostate cancer" as used herein refers to histologically or cytologically confirmed adenocarcinoma of the prostate.

The term "NM-CRPC" as used herein refers to non-metastatic castration-resistant prostate cancer. In some embodiments, NM-CRPC is assessed with bone scan and computed tomography (CT) or magnetic resonance imaging (MRI) scans.

The term "high risk NM-CRPC" as used herein refers to probability of a man with NM-CRPC developing metastases. In some embodiments, high risk for development of metastases is defined as prostate specific antigen doubling time (PSADT) ≤20 months, ≤19 months, ≤18 months, ≤17 months, ≤16 months, ≤15 months, ≤14 months, ≤13 months, ≤12 months, or ≤11 months, ≤10 months, ≤9 months, ≤8 months, ≤7 months, ≤6 months, ≤5 months, ≤4 months, ≤3 months, ≤2 months, or ≤1 month. In some embodiments, high risk for development of metastases is defined as prostate specific antigen doubling time (PSADT) ≤10 months.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an anti-androgen being administered which will relieve to some extent one or more of the symptoms of the disease or condition being treated. The result can be reduction and/or alleviation of the signs, symptoms, or causes of a disease, or any other desired alteration of a biological system. For example, an effective amount of an anti-androgen is the amount of the anti-androgen that after administration for 3 months to a male human with non-metastatic castration-resistant prostate cancer provides a PSA50 or PSA90 or demonstrates a robust (such as ≥90%) AR blockade (e.g. by FDHT-PET). In some embodiments, an effective amount of an anti-androgen is the amount of the anti-androgen that after administration for 6 months to a male human with non-metastatic castration-resistant prostate cancer provides a PSA50 or PSA90. In some embodiments, the anti-androgen is administered on a continuous daily dosing schedule. An appropriate "effective" amount in any individual case may be determined using techniques, such as a dose escalation study.

The term "FDHT-PET" refers to 18F-16β-fluoro-5α-dihydrotestosterone Positron Emission Tomography and is a technique that uses a tracer based on dihydrotestosterone, and allows for a visual assessment of ligand binding to the androgen receptor in a patient. It may be used to evaluate pharmacodynamics of an androgen receptor directed therapy The term "continuous daily dosing schedule" refers to the administration of an anti-androgen daily without any drug holidays. In some embodiments, a continuous daily dosing schedule comprises administration of an anti-androgen everyday at roughly the same time each day.

The terms "treat," "treating" or "treatment," as used herein, include alleviating, abating or ameliorating at least one symptom of a disease disease or condition, preventing additional symptoms, inhibiting the disease or condition, e.g., arresting the development of the disease or condition, relieving the disease or condition, causing regression of the disease or condition, delaying progression of condition, relieving a condition caused by the disease or condition, or stopping the symptoms of the disease or condition either prophylactically and/or therapeutically. In some embodiments, in the context of administering an anti-androgen to a male human with NM-CRPC, treating comprises any one, or a combination, of the following: providing a PSA50 or PSA90 in men with NM-CRPC as compared to placebo at 3 months; providing a PSA50 or PSA90 in men with NM-CRPC as compared to placebo at 6 months; demonstrating superiority in the metastasis-free survivial (MFS) of men with NM-CRPC as compared to placebo (i.e. not administering a second-generation anti-androgen); increasing the overall survisial (OS) of men with NM-CRPC as compared to placebo; increasing the time to metastasis (TTM) in men with NM-CRPC as compared to placebo; increasing the progression-free survival (PFS) in men with NM-CRPC as compared to placebo; increasing the time to PSA progression (TTPP) in men with NM-CRPC as compared to placebo; increasing the health-related quality of life and prostate cancer-specific symptoms in men with NM-CRPC as compared to placebo. In some embodiments, the NM-CRPC is high-risk NM-CRPC.

The term "metastasis-free survival" or "MFS" refers to the the percentage of subjects in a study who have survived without cancer spread for a defined period of time or death. MFS is usually reported as time from the beginning of treatment in the study. MFS is reported for an individual or a study population. In the context of treatment of NM-CRPC with an anti-androgen, an increase in the metastasis-free survival is the additional time that is observed without cancer having spread or death, whichever occurs first, as compared to treatment with placebo. In some embodiments, the increase in the metastasis-free survival is about 1 month, about 2 months, about 2 months, about 3 months, about 4 months, about 5 months, about 6 months, about 7 months, about 8 months, about 10 months, about 11 months, about 12 months, about 13 months, about 14 months, about 15 months, about 16 months, about 17 months, about 18 months, about 19 months, about 20 months, or greater than 20 months.

The term "placebo" as used herein means administration of a pharmaceutical composition that does not include a second-generation anti-androgen. In the context of treatment of NM-CRPC, men that are administered an anti-androgen or placebo will need to continue to maintain castrated levels of testosterone by either coadministration of a GnRH agonist/antagonist or orchiectomy.

Routes of Administration

Suitable routes of administration of the anti-androgen include, but are not limited to, oral or parenteral (e.g., intravenous, subcutaneous, intramuscular). The anti-androgen is administered in the form of a dispersion, solution, suspension, tablet, capsule, or pill. All formulations for oral administration are in dosages suitable for such administration. A summary of pharmaceutical compositions can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

A therapeutically effective amount of an anti-androgen can vary widely depending on the severity of the disease, the age and relative health of the subject, the potency of the anti-androgen used and other factors.

The term "acceptable" with respect to a formulation, composition or ingredient, as used herein, means having no persistent detrimental effect on the general health of the male human being treated.

Methods of Dosing and Treatment Regimens

In one aspect, a second-generation anti-androgen is administered daily to men with NM-CRPC. In some embodiments, the second-generation anti-androgen is orally administered to men with NM-CRPC. In some embodiments, the second-generation anti-androgen is administered once-a-day to men with NM-CRPC. In some embodiments, the second-generation anti-androgen is administered twice-a-day to men with NM-CRPC. In some embodiments, the second-generation anti-androgen is administered three times-a-day to men with NM-CRPC.

In general, doses of a second-generation anti-androgen employed for treatment of NM-CRPC in adult male humans are typically in the range of 10 mg-1000 mg per day. In one embodiment, the desired dose is conveniently presented in a single dose or in divided doses administered simultaneously (or over a short period of time) or at appropriate intervals, for example as two, three, four or more sub-doses per day. In some embodiments, the second-generation anti-androgen is conveniently presented in divided doses that are administered simultaneously (or over a short period of time) once a day. In some embodiments, the second-generation anti-androgen is conveniently presented in divided doses that are administered in equal portions twice-a-day.

In some embodiments, the second-generation anti-androgen is 4-[7-(6-cyano-5-trifluoromethylpyridin-3-yl)-8-oxo-6-thioxo-5,7-diazaspiro[3.4]oct-5-yl]-2-fluoro-N-methylbenzamide. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered daily to the male human. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human at a dose of about 30 mg per day to about 960 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human at a dose of about 30 mg per day to about 480 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human at a dose of about 180 mg per day to about 480 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human at a dose of about 30 mg per day, about 60 mg per day, about 90 mg per day, about 120 mg per day, about 180 mg per day, about 240 mg per day, about 300 mg per day, about 390 mg per day, about 480 mg per day, about 600 mg per day, about 780 mg per day, or about 960 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human at a dose of about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human on a continuous daily dosing schedule.

In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human with NM-CRPC at a dose of about 240 mg per day. In some embodiments, greater than 240 mg per day of 4-[7-(6-cyano-5-trifluoromethylpyridin-3-yl)-8-oxo-6-thioxo-5,7-diazaspiro[3.4]oct-5-yl]-2-fluoro-N-methylbenzamide is administered to the male human with NM-CRPC. In some embodiments, the amount of 4-[7-(6-cyano-5-trifluoromethylpyridin-3-yl)-8-oxo-6-thioxo-5,7-diazaspiro[3.4]oct-5-yl]-2-fluoro-N-methylbenzamide is administered once-a-day. In some other embodiments, the amount of 4-[7-(6-cyano-5-trifluoromethylpyridin-3-yl)-8-oxo-6-thioxo-5,7-diazaspiro[3.4]oct-5-yl]-2-fluoro-N-methylbenzamide is administered twice-a-day.

In some embodiments, 4-(3-(4-cyano-3-(trifluoromethyl)phenyl)-5,5-dimethyl-4-oxo-2-thioxoimidazolidin-1-yl)-2-fluoro-N-methylbenzamide is administered orally to the male human with NM-CRPC at a dose of about 160 mg per day. In some embodiments, greater than 160 mg per day of 4-(3-(4-cyano-3-(trifluoromethyl)phenyl)-5,5-dimethyl-4-oxo-2-thioxoimidazolidin-1-yl)-2-fluoro-N-methylbenzamide is administered orally to the male human with NM-CRPC.

In certain embodiments wherein improvement in the status of the NM-CRPC in the male is not observed, the daily dose of the second-generation anti-androgen is increased. In some embodiments, a once-a-day dosing schedule is changed to a twice-a-day dosing schedule. In some embodiments, a three times a day dosing schedule is employed to increase the amount of second-generation anti-androgen that is administered.

In some embodiments, the amount of the second-generation anti-androgen that is given to the men with NM-CRPC varies depending upon factors such as, but not limited to, the particular second-generation anti-androgen, condition and severity of the NM-CRPC, and the identity (e.g., weight) of the man.

The following listing of Embodiments in intended to complement, rather than displace or supersede, the previous descriptions.

Embodiment 1

A method of treating non-metastatic castration-resistant prostate cancer in a male human comprising administering a therapeutically effective amount of an anti-androgen to a male human with a non-metastatic castration-resistant prostate cancer Embodiment 2

The method of Embodiment 1, wherein the non-metastatic castration-resistant prostate cancer is a high risk non-metastatic castration-resistant prostate cancer.

Embodiment 3

The method of Embodiment 2, wherein the male human with the high risk non-metastatic castration-resistant prostate cancer has a prostate-specific antigen doubling time (PSADT) that is less than or equal to 10 months.

Embodiment 4

The method of any one of Embodiments 1 to 3, wherein administration of the anti-androgen provides an increase in the metastasis-free survival of the male human.

Embodiment 5

A method of providing an increase in the metastasis-free survival of a male human with prostate cancer comprising administering administering a therapeutically effective amount of an anti-androgen to the male human with prostate cancer.

Embodiment 6

The method of Embodiment 5, wherein the prostate cancer is non-metastatic castration-resistant prostate cancer.

Embodiment 7

The method of Embodiment 5, wherein the prostate cancer is high risk non-metastatic castration-resistant prostate cancer.

Embodiment 8

The method of Embodiment 7, wherein the male human with high risk non-metastatic castration-resistant prostate cancer has a prostate-specific antigen doubling time (PSADT) that is less than or equal to 10 months.

Embodiment 9

The method of any one of Embodiments 1 to 8, wherein the anti-androgen is a non-steroidal anti-androgen.

Embodiment 10

The method of any one of Embodiments 1 to 9, wherein the anti-androgen binds directly to the ligand-binding domain of the androgen receptor.

Embodiment 11

The method of any one of Embodiments 1 to 10, wherein the anti-androgen is a second-generation anti-androgen.

Embodiment 12

The method of any one of Embodiments 1 to 11, wherein the anti-androgen is 4-[7-(6-cyano-5-trifluoromethylpyridin-3-yl)-8-oxo-6-thioxo-5,7-diazaspiro[3.4]oct-5-yl]-2-fluoro-N-methylbenzamide; 4-(3-(4-cyano-3-(trifluoromethyl)phenyl)-5,5-dimethyl-4-oxo-2-thioxoimidazolidin-1-yl)-2-fluoro-N-methylbenzamide (enzalutamide); or 4-[7-(4-cyano-3-trifluoromethylphenyl)-8-oxo-6-thioxo-5,7-diazaspiro[3.4]oct-5-yl]-2-fluoro-N-methylbenzamide (RD162).

Embodiment 13

The method of any one of Embodiments 1 to 12, wherein the anti-androgen is 4-[7-(6-cyano-5-trifluoromethylpyridin-3-yl)-8-oxo-6-thioxo-5,7-diazaspiro[3.4]oct-5-yl]-2-fluoro-N-methylbenzamide.

Embodiment 14

The method of Embodiment 13, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide is administered daily to the male human.

Embodiment 15

The method of Embodiment 13 or 14, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human.

Embodiment 16

The method of any one of Embodiments 13 to 15, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human at a dose of about 30 mg per day to about 480 mg per day.

Embodiment 17

The method of any one of Embodiments 13 to 15, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human at a dose of about 180 mg per day to about 480 mg per day.

Embodiment 18

The method of any one of Embodiments 13 to 15, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human at a dose of about 30 mg per day, about 60 mg per day, about 90 mg per day, about 120 mg per day, about 180 mg per day, about 240 mg per day, about 300 mg per day, about 390 mg per day, or about 480 mg per day.

Embodiment 19

The method of any one of Embodiments 13 to 15, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human at a dose of about 240 mg per day.

Embodiment 20

The method of any one of Embodiments 13 to 19, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human on a continuous daily dosing schedule.

EXAMPLES

These examples are provided for illustrative purposes only and not to limit the scope of the claims provided herein.

Example 1: Phase III Clinical Trial of 4-[7-(6-Cyano-5-trifluoromethylpyridin-3-yl)-8-oxo-6-thioxo-5,7-diazaspiro[3.4]oct-5-yl]-2-fluoro-N-methylbenzamide in Men with Non-Metastatic Castration-Resistant Prostate Cancer (NM-CRPC)

This is a randomized, multicenter, double-blind, Phase III clinical trial evaluating the efficacy and safety of 4-[7-(6-cyano-5-trifluoromethylpyridin-3-yl)-8-oxo-6-thioxo-5,7-diazaspiro[3.4]oct-5-yl]-2-fluoro-N-methylbenzamide (treatment arm A) versus placebo (treatment arm B) in men with high risk NM-CRPC, defined as PSA Doubling Time (PSADT) ≤10 months. All men participating in the clinical trial should maintain castrated levels of testosterone (<50 ng/dL [1.72 nmol/L]) by continuous administration of a GnRH agonist or antagonist, or by orchiectomy.

4-[7-(6-Cyano-5-trifluoromethylpyridin-3-yl)-8-oxo-6-thioxo-5,7-diazaspiro[3.4]oct-5-yl]-2-fluoro-N-methylbenzamide will be administered orally on a continuous daily dosing schedule, at a starting dose of 240 mg per day in treatment arm A. Matched placebo will be administered orally on a continuous daily dosing schedule, at a starting dose of 240 mg per day in treatment arm B.

Patients will be followed for safety and efficacy as per the schedule of assessments and will remain on study treatment until documented progression (development of metastases as assessed by blinded independent central review) or unacceptable toxicity.

Patients discontinuing treatment due to disease progression will be followed for survival and subsequent anticancer therapies every 4 months until death, loss of follow-up, or withdrawal of consent, whichever comes first.

Patients discontinuing treatment prior to disease progression will continue to have scheduled disease assessments until progression, initiation of a subsequent anticancer therapy in the absence of documented disease progression, withdrawal of consent, loss of follow-up, or until death, whichever comes first.

Endpoints

The primary endpoint is metastasis-free survival (MFS).

The secondary endpoints include overall survival (OS); time to metastasis (TTM); progression-free survival (PFS); health-related quality of life and prostate cancer-specific symptoms; type, incidence, severity, timing, seriousness, and relatedness of adverse events and laboratory abnormalities; pharmacokinetics parameters.

Target Population

Inclusion Criteria

1. Histologically or cytologically confirmed adenocarcinoma of the prostate without neuroendocrine differentiation or small cell features, with high risk for development of metastases, defined as PSADT ≤10 months
2. Castration-resistant prostate cancer demonstrated during continuous androgen deprivation therapy (ADT)/post orchiectomy, defined as 3 consecutive rises of PSA, 1 week apart, resulting in two 50% increases over the nadir, with the last PSA >2 ng/mL
3. Maintain castrate levels of testosterone (<50 ng/dL [1.72 nmol/L]) within 4 weeks of randomization and throughout the study
4. Patients currently receiving bone loss prevention treatment with bone-sparing agents (e.g., bisphosphonates, denosumab [Prolia®]) must be on stable doses for at least 4 weeks prior to randomization
5. Patients who received a first generation anti-androgen (e.g., bicalutamide, flutamide, nilutamide) as part of an initial combined androgen blockade therapy or as second-line hormonal therapy must show continuing disease (PSA) progression off the anti-androgen for at least 4 weeks prior to randomization
6. At least 4 weeks must have elapsed from the use of 5-α reductase inhibitors (e.g., dutasteride, finasteride, aminoglutethamide), estrogens, and any other anticancer therapy prior to randomization, including chemotherapy given in the adjuvant/neoadjuvant setting (e.g., clinical trial)
7. At least 4 weeks must have elapsed from major surgery or radiation therapy prior to randomization
8. Age ≥18 years
9. Eastern Cooperative Oncology Group (ECOG) Performance Status 0 or 1
10. Resolution of all acute toxic effects of prior therapy or surgical procedure to Grade ≤1 or baseline prior to randomization
11. Adequate organ function as defined by the following criteria:
    Serum aspartate transaminase (AST; serum glutamic oxaloacetic transaminase [SGOT]) and serum alanine transaminase (ALT; serum glutamic pyruvic transaminase [SGPT]) ≤2.5× upper limit of normal (ULN)
    Total serum bilirubin ≤1.5×ULN
    Serum creatinine ≤2×ULN
    Absolute neutrophil count (ANC) ≥1500/μL
    Platelets ≥100,000/μL
    Hemoglobin ≥9.0 g/dL
    Administration of growth factors or blood transfusions will not be allowed within 4 weeks of the hematology labs required to confirm eligibility
12. Signed and dated informed consent document indicating that the patient (or legally acceptable representative) has been informed of all pertinent aspects of the trial prior to randomization
13. Willingness and ability to comply with scheduled visits, treatment plans, laboratory and radiographic assessments, and other study procedures, including ability to swallow large capsules, the completion of patient reported outcomes questionnaires and long-term survival follow-up visits Exclusion Criteria 1. Presence of distant metastases, including CNS and vertebral or meningeal involvement. Exception: pelvic lymph nodes <2 cm in short axis (N1) located below the iliac bifurcation are allowed
2. Symptomatic loco-regional disease requiring medical intervention, such as moderate or severe urinary obstruction or hydronephrosis due to primary tumor (e.g., tumor obstruction of bladder trigone)
3. Prior treatment with second-generation antiandrogens (e.g., enzalutamide)
4. Prior treatment with CYP17 inhibitors (e.g., abiraterone acetate, orteronel, galeterone, ketoconazole)
5. Prior treatment with radiopharmaceutical agents (e.g., Strontium-89), immunotherapy (e.g., sipuleucel-T) or any other investigational agent for NM-CRPC
6. Prior chemotherapy, except if administered in the adjuvant/neoadjuvant setting
7. History of seizure or condition that may pre-dispose to seizure (e.g., prior stroke within 1 year prior to randomization, brain arteriovenous malformation, Schwannoma, meningioma, or other benign CNS or meningeal disease which may require treatment with surgery or radiation therapy)
8. Concurrent therapy with any of the following (all must have been discontinued or substituted for at least 4 weeks prior to randomization):
    Medications known to lower the seizure threshold
    Herbal and non-herbal products that may decrease PSA levels (i.e., saw palmetto, pomegranate juice)
    Systemic (oral/IV/IM) corticosteroids. Short term use (≤4 weeks) of corticosteroids during the study is allowed if clinically indicated, but it should be tapered off as soon as possible
    Any other experimental treatment on another clinical trial
9. History or evidence of any of the following conditions:
    Any prior malignancy (other than adequately treated basal cell or squamous cell skin cancer, superficial bladder cancer, or any other cancer in situ currently in complete remission) within 5 years prior to randomization
    Severe/unstable angina, myocardial infarction, symptomatic congestive heart failure, arterial or venous thromboembolic events (e.g., pulmonary embolism, cerebrovascular accident including transient ischemic attacks), or clinically significant ventricular arrhythmias within 6 months prior to randomization Uncontrolled hypertension (≥160 mmHg systolic blood pressure and/or diastolic blood pressure ≥100 mmHg)

Gastrointestinal disorder affecting absorption

Active infection, such as human immunodeficiency virus (HIV)

Any other condition that, in the opinion of the Investigator, would impair the patient's ability to comply with study procedures Assessment Schedule Safety Assessment Plan Patients will be assessed for adverse events at each monthly clinic visit while on the study. Adverse events will be graded according to the NCI Common Terminology Criteria for Adverse Events (CTCAE) Version 4.0. Adverse events will be assessed by the investigator as related or not related to study drug. Dose interruptions and/or reductions to the next lower dose level will be permitted as needed, provided that study discontinuation criteria have not been met (e.g., documented disease progression or unacceptable toxicity, such as seizure).

An independent third-party Data Monitoring Committee (DMC) will monitor the safety of the patients, with meetings at least twice per year to determine overall safety and benefit:risk assessment. Periodic quarterly adverse event data review will also be performed by designated members of the sponsor's primary study team and will be blinded to treatment assignment with adverse event from both treatment groups combined. Any safety issues of concern identified by the primary study team will be promptly reported to the DMC, as per the DMC charter.

As those skilled in the art will appreciate, numerous modifications and variations of the present invention are possible in light of these teachings, and all such are contemplated hereby. For example, in addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document are hereby incorporated herein by reference, each in its entirety, for all purposes.

What is claimed is:

1. A method of treating non-metastatic castration-resistant prostate cancer in a male human comprising administering an anti-androgen at a dose of about 30 mg per day to about 480 mg per day to a male human in need of such treatment, wherein the anti-androgen is 4-[7-(6-cyano-5-trifluoromethylpyridin-3-yl)-8-oxo-6-thioxo-5,7-diazaspiro[3.4]oct-5-yl]-2fluoro-N-methylbenzamide, and wherein said method further comprises orchiectomy.

2. The method of claim 1, wherein the non-metastatic castration-resistant prostate cancer is a high risk non-metastatic castration-resistant prostate cancer.

3. The method of claim 1, wherein the 4-[7 (6 cyano-5-trifluoromethylpyridin-3-yl)-8-oxo-6-thioxo-5,7-diazaspiro[3.4]oct-5-yl]-2fluoro-N-methylbenzamide is administered orally to the male human.

4. The method of claim 1, wherein the 4-[7-(6-cyano-5-trifluoromethylpyridin-3-yl)-8-oxo-6-thioxo-5,7-diazaspiro[3.4]oct-5-yl]-2fluoro-N-methylbenzamide is administered post orchiectomy.

5. The method of claim 1, wherein the 4-[7-(6-cyano-5-trifluoromethylpyridin-3-yl)-8-oxo-6-thioxo-5,7-diazaspiro[3.4]oct-5-yl]-2fluoro-N-methylbenzamide is administered daily to the male human.

6. The method of claim 1, wherein the 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human at a dose of about 180 mg per day to about 480 mg per day.

7. The method of claim 1, wherein the 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human at a dose of:
  (a) about 30 mg per day;
  (b) about 60 mg per day;
  (c) about 90 mg per day;
  (d) about 120 mg per day; or
  (e) about 240 mg per day.

8. The method of claim 1, wherein the 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human at a dose of about 240 mg per day.

9. The method of claim 1, wherein the 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human on a continuous daily dosage schedule.

10. A method of treating non-metastatic castration-resistant prostate cancer in a male human consisting essentially of administering an anti-androgen at a dose of about 30 mg per day to about 480 mg per day to a male human in need of such treatment, wherein the anti-androgen is 4-[7-(6-cyano-5-trifluoromethylpyridin-3-yl)-8-oxo-6-thioxo-5,7-diazaspiro[3.4]oct-5-yl]-2-fluoro-N-methylbenzamide, and wherein said method further comprises orchiectomy.

11. The method of claim 10, wherein the 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human at a dose of:
  (a) about 30 mg per day;
  (b) about 60 mg per day;
  (c) about 90 mg per day;
  (d) about 120 mg per day; or
  (e) about 240 mg per day.

12. The method of claim 10, wherein the 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human at a dose of about 240 mg per day.

13. The method of claim 10, wherein the 4-[7-(6-cyano-5-trifluoromethylpyridin-3-yl)-8-oxo-6-thioxo-5,7-diazaspiro[3.4]oct-5-yl]-2fluoro-N-methylbenzamide is administered post orchiectomy.

14. The method of claim 10, wherein the male human with the high risk non-metastatic castration-resistant prostate cancer has a prostate-specific antigen doubling time (PSADT) that is less than or equal to 10 months.

15. The method of claim 1, wherein administration of the anti-androgen provides an increase in the metastasis-free survival of the male human, relative to the mean survival rate of a population of male humans with the non-metastatic castration-resistant prostate cancer, said population having been treated with a placebo.

\* \* \* \* \*